(12) United States Patent
Langley et al.

(10) Patent No.: US 7,824,355 B2
(45) Date of Patent: *Nov. 2, 2010

(54) METHODS AND DEVICES FOR PROCESSING BLOOD

(75) Inventors: Robert W. Langley, Westminster, CO (US); Thomas J. Felt, Boulder, CO (US); Geert Van Waeg, Brussels (BE); Marlene Adele Bainbridge, Golden, CO (US)

(73) Assignee: CaridianBCT, Inc., Lakewood, CO (US)

( * ) Notice: Subject to any disclaimer, the term of this patent is extended or adjusted under 35 U.S.C. 154(b) by 166 days.

This patent is subject to a terminal disclaimer.

(21) Appl. No.: 12/187,988

(22) Filed: Aug. 7, 2008

(65) Prior Publication Data

US 2009/0043237 A1   Feb. 12, 2009

Related U.S. Application Data

(63) Continuation of application No. 10/680,950, filed on Oct. 8, 2003, now Pat. No. 7,704,454.

(51) Int. Cl.
*A61M 37/00* (2006.01)
*A61M 1/00* (2006.01)
*A61M 5/00* (2006.01)

(52) U.S. Cl. ............... 604/4.01; 604/5.01; 604/6.16; 604/27; 604/118; 604/119; 422/44

(58) Field of Classification Search ............ 604/4.01, 604/5.01, 6.16, 27, 118, 119; 422/44
See application file for complete search history.

(56) References Cited

U.S. PATENT DOCUMENTS

| | | | |
|---|---|---|---|
| 3,655,123 A | 4/1972 | Judson et al. | |
| 3,709,222 A | 1/1973 | DeVries | |
| 3,946,731 A | 3/1976 | Lichtenstein | |
| 4,024,483 A | 5/1977 | Tomczak et al. | |
| 4,080,966 A | 3/1978 | McNally et al. | |

(Continued)

FOREIGN PATENT DOCUMENTS

| | | |
|---|---|---|
| EP | 0834329 | 4/1998 |
| WO | WO 00/12991 | 3/2000 |

OTHER PUBLICATIONS

Baxter Healthcare Corporation, *CS-3000 Plus Parameter Changes, Operator's Manual*, Chapter 1, "Description"' Chapter 4, "Warnings"; Chapter 5, Precautions; Chapter 8, "Information for Use"; Chapter 9, "Run Procedures"'; Chapter 12, "Troubleshooting", pp. 12-12 through 12-36 (undated, in use 1 year prior to filing).

(Continued)

*Primary Examiner*—Leslie R. Deak
*Assistant Examiner*—Adam Marcetich
(74) *Attorney, Agent, or Firm*—Greenlee Sullivan PC

(57) ABSTRACT

Methods, devices and device components are presented for blood processing. Particularly, methods, devices and device components are presented for separating blood into blood components and collecting one or more separated blood components, which reduce the incidence of blood vessel infiltration and enhance donor comfort. In one aspect, the invention provides blood processing methods having a return flow rate which decreases systematically during a return time. In another aspect, the invention provides blood processing methods having a removal flow rate, return flow rate or both which are derived from a subject's total blood volume. In another aspect, the present invention provides blood processing methods wherein the fraction by volume of removed blood corresponding to collected components is selected to optimize blood processing efficiency and enhance the purities of collected blood components.

27 Claims, 8 Drawing Sheets

U.S. PATENT DOCUMENTS

| | | | |
|---|---|---|---|
| 4,086,924 A | 5/1978 | Latham, Jr. | |
| 4,146,172 A | 3/1979 | Cullis et al. | |
| 4,148,314 A | 4/1979 | Yin | |
| 4,174,637 A | 11/1979 | Mulzet et al. | |
| 4,185,629 A | 1/1980 | Cullis et al. | |
| 4,227,420 A | 10/1980 | Lamadrid | |
| 4,231,366 A | 11/1980 | Schael | |
| 4,263,808 A | 4/1981 | Bellotti et al. | |
| 4,285,464 A | 8/1981 | Latham, Jr. | |
| 4,370,983 A * | 2/1983 | Lichtenstein | 600/301 |
| 4,385,630 A | 5/1983 | Gilcher et al. | |
| 4,425,114 A | 1/1984 | Schoendorfer et al. | |
| 4,436,620 A | 3/1984 | Bellotti et al. | |
| 4,468,219 A | 8/1984 | George et al. | |
| 4,479,761 A | 10/1984 | Bilstad et al. | |
| 4,501,531 A | 2/1985 | Bilstad et al. | |
| 4,637,813 A | 1/1987 | DeVries | |
| 4,657,529 A * | 4/1987 | Prince et al. | 604/6.11 |
| 4,661,246 A | 4/1987 | Ash | |
| 4,710,164 A | 12/1987 | Levin et al. | |
| 4,718,891 A | 1/1988 | Lipps | |
| 4,739,492 A | 4/1988 | Cochran | |
| 4,798,090 A | 1/1989 | Heath et al. | |
| 4,828,543 A | 5/1989 | Weiss et al. | |
| 4,850,998 A | 7/1989 | Schoendorfer | |
| 4,883,462 A | 11/1989 | Williamson et al. | |
| 4,911,703 A | 3/1990 | Lysaght et al. | |
| 4,923,439 A | 5/1990 | Seidel et al. | |
| 5,069,792 A | 12/1991 | Prince et al. | |
| 5,120,303 A | 6/1992 | Hombrouckx | |
| 5,171,212 A | 12/1992 | Buck et al. | |
| 5,174,894 A | 12/1992 | Ohsawa et al. | |
| 5,186,431 A | 2/1993 | Tamari | |
| 5,200,090 A | 4/1993 | Ford et al. | |
| 5,211,849 A * | 5/1993 | Kitaevich et al. | 604/5.04 |
| 5,370,123 A | 12/1994 | Shinzato | |
| 5,372,709 A | 12/1994 | Hood | |
| 5,431,811 A | 7/1995 | Tusini et al. | |
| 5,437,624 A | 8/1995 | Langley | |
| 5,487,827 A | 1/1996 | Peterson et al. | |
| 5,499,648 A | 3/1996 | Powell et al. | |
| 5,501,665 A | 3/1996 | Jhuboo et al. | |
| 5,536,237 A * | 7/1996 | Prince et al. | 604/6.11 |
| 5,555,910 A | 9/1996 | Powell et al. | |
| 5,618,441 A | 4/1997 | Rosa et al. | |
| 5,647,984 A | 7/1997 | Hovland et al. | |
| 5,653,887 A | 8/1997 | Wahl et al. | |
| 5,690,831 A | 11/1997 | Kenley et al. | |
| 5,690,835 A * | 11/1997 | Brown | 210/739 |
| 5,711,883 A | 1/1998 | Folden et al. | |
| 5,762,805 A | 6/1998 | Truitt et al. | |
| 5,776,345 A | 7/1998 | Truitt et al. | |
| 5,795,317 A | 8/1998 | Brierton et al. | |
| 5,806,553 A | 9/1998 | Sidwell | |
| 5,827,223 A | 10/1998 | Butterfield | |
| 5,837,150 A | 11/1998 | Langley et al. | |
| 5,906,570 A | 5/1999 | Langley et al. | |
| 5,906,589 A | 5/1999 | Gordon et al. | |
| 5,910,252 A | 6/1999 | Truitt et al. | |
| 5,913,768 A | 6/1999 | Langley et al. | |
| 5,919,154 A | 7/1999 | Toavs et al. | |
| 5,921,950 A | 7/1999 | Toavs et al. | |
| 5,941,842 A | 8/1999 | Steele et al. | |
| 5,954,971 A | 9/1999 | Pages et al. | |
| 5,980,465 A * | 11/1999 | Elgas | 600/504 |
| 5,992,449 A | 11/1999 | Sprague | |
| 6,007,725 A * | 12/1999 | Brown | 210/739 |
| 6,033,561 A | 3/2000 | Schoendorfer | |
| 6,053,856 A | 4/2000 | Hlavinka | |
| 6,200,485 B1 * | 3/2001 | Kitaevich et al. | 210/739 |
| 6,296,450 B1 * | 10/2001 | Westberg et al. | 417/18 |
| 6,451,203 B2 * | 9/2002 | Brown | 210/143 |
| 6,471,872 B2 * | 10/2002 | Kitaevich et al. | 210/739 |
| 6,613,009 B1 | 9/2003 | Bainbridge et al. | |
| 6,780,322 B1 * | 8/2004 | Bissler et al. | 210/637 |
| 2001/0045395 A1 * | 11/2001 | Kitaevich et al. | 210/739 |
| 2001/0048892 A1 * | 12/2001 | Bainbridge et al. | 422/44 |
| 2002/0062100 A1 * | 5/2002 | Pierce et al. | 604/6.01 |
| 2004/0030277 A1 * | 2/2004 | O'Mahony et al. | 604/4.01 |

OTHER PUBLICATIONS

COBE BCT, Inc. COBE Spectra Apheresis System, Operator's Manual, "Table of Contents"; Section 1 "Introduction"; Section 4A, "Platelet Dual-Needle Operation"; Section 9, "Diagnostics" (1991).

European Search Report for corresponding foreign application No. 00311669.6 dated Jul. 21, 2003.

Fresenius Operation Manual, *Fresenius MT AS 104 Blood Cell Separator*, Section 3 "Safety and Alarm Circuits: Section 4," Remedies in Case of Alarm or Error Conditions; Section 6, "Definitions and Terms"; Section 7, "Tablesand Figures" (1990).

Schoendorfer, D.W.; "Automation in Apheresis" pp. 129-146 (undated, in use 1 year prior to filing).

* cited by examiner

METHODS AND DEVICES FOR PROCESSING BLOOD

CROSS REFERENCE TO RELATED APPLICATIONS

This application is a Continuation of U.S. application Ser. No. 10/680,950, filed Oct. 08, 2003, which issued as U.S. Pat. No. 7,704,454 on Apr. 27, 2010, which is incorporated in its entirety herein to the extent that there is no inconsistency with the present disclosure.

BACKGROUND OF INVENTION

Collection, processing and purification of biological samples are important processes in a range of medical therapies and procedures. Important biological samples used as therapeutic agents include whole blood and its various purified blood components, such as red blood cells, white blood cells and plasma. In the field of transfusion medicine, one or more whole blood components are directly introduced into a patient's blood stream to replace a depleted or deficient component. Infusion of plasma-derived materials, such as blood proteins, also plays a critical role in a number of therapeutic applications. For example, plasma-derived immunoglobulin is commonly provided to supplement a patient's compromised immune system. Due to increases in the demand for purified biological samples for transfusion, infusion and transplantation therapies, substantial research efforts have been directed at improving the availability, safety and purity of biological samples used as therapeutic agents.

In conventional large scale blood collection, blood is removed from a donor or patient, separated into its various blood components via centrifugation, filtration and/or elutriation and stored in sterile containers for future infusion into a patient for therapeutic use. The separated blood components typically include fractions corresponding to red blood cells, white blood cells, platelets and plasma. Separation of blood into its components may be performed continuously during collection or may be performed subsequent to collection in batches, particularly with respect to the processing of whole blood samples. Separation of blood into its various components under highly sterile conditions is crucial for a wide variety of therapeutic applications.

Recently, apheresis blood collection techniques have been widely adopted in large scale blood collection centers wherein a selected component of blood or plurality of blood components are collected and the balance of the blood is returned to the donor during collection. In apheresis, blood is removed from a donor and immediately separated into its components by on-line blood processing methods. Typically, such on-line blood processing is provided by density centrifugation, filtration and diffusion-based separation techniques. One or more of the separated blood components are collected and stored in sterile containers, while the remaining blood components are directly recirculated to the donor. An advantage of this method is that it allows more frequent donation from an individual donor because only a selected blood component is collected and purified. For example, a donor undergoing plateletpheresis, whereby platelets are collected and the non-platelet blood components are returned to the donor, may donate blood as often as once per week.

Apheresis blood processing also plays an important role in a large number of therapeutic procedures. In these methods, blood is withdrawn from a patient undergoing therapy, separated, and a selected fraction is collected while the remainder is returned to the patient. For example, a patient may undergo leukapheresis prior to radiation therapy, whereby the white blood cell component of his blood is separated, collected and stored to avoid exposure to radiation. Alternatively, apheresis techniques may be used to perform red blood cell exchange for patients with hematological disorders such as sickle cell anemia and thalassemia, whereby the patient's red blood cell component is removed and donated packed red blood cells are provided to the patient along with his remaining blood components. Further, apheresis may be used to perform therapeutic platelet depletion for patients having thrombocytosis and therapeutic plasma exchange for patients with autoimmune diseases.

Both conventional blood collection and apheresis systems typically employ differential centrifugation methods for separating blood into its various blood components. In differential centrifugation, blood is circulated through a sterile separation chamber which is rotated at high rotational speeds about a central rotation axis. Rotation of the separation chamber creates a centrifugal force directed along rotating axes of separation oriented perpendicular to the central rotation axis of the centrifuge. The centrifugal field generated upon rotation separates particles suspended in the blood sample into discrete fractions accordingly to density. Specifically, a blood sample separates into discrete phases corresponding to a higher density fraction comprising red blood cells and a lower density fraction comprising plasma. In addition, an intermediate density fraction comprising platelets and leukocytes forms an interface layer between the red blood cells and the plasma. Descriptions of blood centrifugation devices are provided in U.S. Pat. No. 5,653,887, which is hereby incorporated in its entireties by reference to the extent it is not inconsistent with the present application.

Despite the demonstrated effectiveness of apheresis blood processing in automated blood donation and in a large number of therapies, several practical limitations remain affecting the practice of these methods. In particular, the occurrence of blood vessel infiltration caused by rapid changes in access blood vessel pressure is a common problem experienced by virtually all apheresis methods known in the art. Although the incidence of blood vessel infiltration is dependent on the particular physiology and anatomy of the subject undergoing a selected blood processing procedure, conventional apheresis systems exhibit on average an incidence of blood vessel infiltration typically greater than or equal to about 4.5%. This correspond to a very significant occurrence of infiltration; about 1 out of every 20 apheresis procedures.

During infiltration, the pressure exerted on the walls of an access blood vessel, such as an access vein, increases or decreases due to the flow of blood or blood components into or out of the subject of a blood processing procedure. To reduce the pressure, the access blood vessel may expand or contract at a rate depending on the size and elasticity of the vessel. In some instances, however, the change in pressure is too great or delivered over a very short time interval and, thus, the access blood vessel cannot accommodate the change in pressure and the change in pressure may result in blood vessel infiltration. For example, a sharp increase in blood vessel pressure over a short time may cause a perforation in the wall of the blood vessel, commonly referred to as vein "blow out." Also, a sharp decrease in blood vessel pressure over a short time may cause the walls of the blood vessel to collapse. Finally, rapid changes in the direction of change in blood vessel pressure may also result in damage to the walls of an access blood vessel.

Blood vessel infiltration has a number of significant deleterious affects on extracorporeal blood processing. First, infiltration may cause injury to the patient or subject undergoing a blood processing procedure. For example, infiltration may result in a hematoma or a change in blood pressure. In addition, infiltration may trigger a cascade of more serious health problems, such as cardiac arrest or embolism. Second, infiltration causes serious pain for the donor or patient undergoing a blood processing procedure. This negatively impacts patient or donor satisfaction with a given blood processing procedure and may affect a donor's decision to donate blood or blood components on a regular basis. Third, infiltration results in a substantial decrease in the flow rate of blood or blood components into or out of a patient or donor. This reduction in flow results in blood processing delay or may result in termination of a selected blood processing procedure. Finally, the risk of infiltration associated with these procedures increases the need for operator or physician intervention and, thus, reduces efficiency and substantially adds to the costs of blood donation or apheresis therapies.

It will be appreciated from the foregoing that a clear need exists for methods and devices for processing blood and blood components having a reduced risk of infiltration. Specifically, apheresis methods and devices are needed which enhance patient or donor comfort and reduce the change in vein pressure experienced during removal and return of blood and blood components during extracorporeal blood processing. Finally, automated methods and devices of apheresis blood processing are needed which require less operator or physician intervention.

SUMMARY OF THE INVENTION

This invention provides methods, devices and device components for processing biological samples, such as bodily fluids. Particularly, the present invention provides methods of blood processing for collecting one or more separated blood components from blood removed from a patient or blood donor. It is an object of the present invention to provide methods and devices for processing blood which minimize changes in the pressure of an access blood vessel and suppress the incidence of access blood vessel infiltration. It is further an object of the present invention to provide methods and devices which reduce physical discomfort experienced by a patient or donor undergoing extracorporeal blood processing. It is yet another object of the present invention to provide methods and devices for blood processing which enhance the purities of separated blood components and optimize the efficiency of blood processing, particularly blood component collection.

In one aspect, the present invention provides blood processing methods and devices having a return flow rate which varies systematically as a function of time. In an exemplary method of the present invention, blood is removed from a subject for a removal time at a selected removal flow rate, thereby generating removed blood. The removed blood is processed, for example by density centrifugation, centrifugal elutriation, size and shape filtration, affinity chromatography or any combination of these techniques, thereby generating processed blood including at least one return component. Typically, processing also generates one or more collect components which are collected. At least a portion of the return component is subsequently returned to the subject over a return time at a selected return flow rate, which is systematically varied over the return time. The return flow rate may be systematically varied with respect to time in any manner resulting in more efficient blood processing, enhanced donor comfort and/or reduced access blood vessel infiltration including, but not limited to, a substantially linear variation, a substantially exponential variation, substantially logarithmic variation and a substantially quadratic variation. In an exemplary embodiment particularly beneficial for minimizing changes in the pressure of an access blood vessel, such as an access vein, the return flow rate is controlled such that it decreases throughout the return time, preferably decreasing in a substantially linear manner. Minimizing changes in the pressure exerted on the walls of an access vein or on an access needle operationally connected to an access vein is beneficial because it reduces the incidence of blood vessel infiltration, hematomas and access needle dislocation during the return of blood components to a patient or donor undergoing a blood processing procedure. In addition, minimizing changes in vein pressure significantly improves patient or donor comfort over conventional extracorporeal blood processing methods. The extracorporeal blood processing methods and devices of the present invention may also provide a removal flow rate which varies systematically as a function of time. In one embodiment useful for minimizing changes in the pressure of an access blood vessel, such as an access vein, the removal flow rate is controlled such that it systematically increases over the return time, preferably increasing in a substantially linear manner.

In another embodiment of the present invention, removal flow rates, return flow rates or both are held substantially constant during selected removal times or return times, but are varied stepwise for repeated draw and return cycles. In this embodiment, blood is removed from a subject for a removal time during a draw cycle at a selected removal flow rate, thereby generating removed blood. The removed blood is processed, thereby generating processed blood including at least one return component. Typically, processing also generates one or more collect component which are collected. At least a portion of the return component is returned to the subject for a return time during a return cycle at a selected return flow rate. Optionally, the return component may be conducted through a fixed volume or variable volume return reservoir prior to return to the subject. In this embodiment, draw and return cycles are sequentially repeated during a selected blood processing time, whereby blood and/or blood components are cyclically removed, cyclically accumulated in the reservoir and cyclically pumped back to the subject. Draw and return cycles are sequentially repeated to achieve a selected extent and duration of blood processing. In an embodiment of the present invention, the removal flow rate, return flow rate or both are varied incrementally in successive removal and/or return cycles. In an embodiment of the present invention useful for avoiding vein collapse, needle dislocation and unwanted reduction in blood removal flow rates, the removal flow rate is incrementally increased by a selected flow rate increment each draw cycle until reaching a maximum removal flow rate, after which the removal flow rate is held constant for successive draw cycles. In this manner, the removal flow rate is stepwise increased over a time interval of about 5 to 25 minutes. Incremental adjustment of removal flow rates for successive draw cycles is beneficial for reducing access needle dislocation, optimizing accommodation of an access needle by an access blood vessel and avoiding blood processing delays caused by unwanted reduction of removal flow rates. Further, incremental adjustment of removal flow rates for successive draw cycles optimizes patient or donor comfort. The present invention also includes embodiments wherein return flow rates are incrementally increased for successive return cycles to optimize donor comfort, avoid blood vessel infiltration and minimize access needle dislocation.

In another aspect, the present invention provides blood processing methods and devices having removal flow rates, return flow rates, or both which are derived from the total blood volume of the subject undergoing extracorporeal blood processing. In an exemplary method of the present invention, blood is removed at a selected removal flow rate, which is derived from the total blood volume of the subject undergoing a blood processing procedure. Removed blood is processed, for example by density centrifugation, centrifugal elutriation, size and shape filtration, affinity chromatography or any combination of these techniques, thereby generating processed blood including at least one return component. Typically, processing also results in generation of one or more collect component which is collected. At least a portion of the return component is returned to the subject at a selected return flow rate, which may also be derived from the total blood volume of the subject. In an embodiment of the present invention providing enhanced donor or patient comfort and blood processing efficiency, the return flow rate, removal flow rate or both are determined by a mathematical relationship involving total blood volume, wherein larger return and/or removal flow rates are employed for subjects having larger total blood volumes. In an embodiment of the present invention providing an approximately 30% reduction in the incidence of blood vessel infiltration as compared to conventional methods of extracorporeal blood processing, return flow rates and removal flow rates are determined by a mathematical relationship wherein both the removal flow rate and return flow rate increase in a substantially linear manner with respect to total blood volume. More particularly, return and removal flow rates of this embodiment increase linearly until reaching a return flow maximum and a removal flow maximum, respectively, wherein the extent of hemolysis during blood processing is less than about 0.1%.

Return flow rates and removal flow rates useable in this aspect of the invention may be substantially constant during removal times, return times or both. Alternatively, removal flow rates and return flow rates may vary systematically during the removal times, return times or both respectively, in a manner which varies as a function of a subjects total blood volume. For example, return and removal flow rates may be ramped to a maximum value which is derived from a subject's total blood volume, or may be ramped at a rate which is proportional to a subject's total blood volume or both.

The present invention includes embodiments having return flow rates and removal flow rates which are defined by non-linear correlations with respect to total blood volume including, but not limited to, substantially exponential, logarithmic and quadratic correlations. In an embodiment of the present invention exhibiting minimized hemolysis during blood processing, return and removal flow rates are controlled in a manner such that they do not exceed threshold return and removal flow rates, which are selected such that the extent of hemolysis is less than 0.1%. In another embodiment, a plurality of removal flow rates, return flow rates or both are provided for each value of total blood volume of a subject and the rates employed during processing are selected in a manner optimizing donor comfort and minimizing the incidence of access blood vessel infiltration and overall blood processing time. In this embodiment, selection of the removal and return flow rates from the plurality of values for each total blood volume value may be determined empirically by monitoring the comfort and physical condition of a subject undergoing processing or may be selected on the basis of the experience of the operator of the blood processing system.

In another aspect, the present invention provides methods and devices for blood processing, which increase the efficiency of blood component separation and collection and enhance the purities of collected blood components. Particularly, methods and devices of the present invention optimize collection efficiency while preventing contamination of collected components with red blood cells. In an exemplary embodiment especially well suited for blood processing using a single needle access configuration, blood is removed from a subject during a draw cycle for a removal time, thereby generating removed blood. Optionally, an anticoagulant agent may be added to the removed blood, thereby generating anticoagulant-treated removed blood. The removed blood or anticoagulant-treated removed blood is conducted through a blood separation system, for example a density centrifuge, centrifugal elutriation system, filter, affinity column or any combination of these separation devices, thereby generating a plurality of separated blood components including at least one collect component. At least a first fraction by volume of the removed blood or anticoagulant-treated removed blood is collected corresponding to a collect component. A second portion of the removed blood corresponding to recirculated component is recirculated through the blood separation system. A third portion of the removed blood corresponding to a returned component is returned to the subject during a return cycle. Optionally, the second and third portions of removed blood may be conducted through a fixed volume or variable volume return reservoir prior to recirculation and/or return to the subject. Draw and return cycles are successively repeated for a selected blood processing time selected to accumulate a desired amount of collected blood components or achieve a desired extent of blood processing. In this embodiment of the present invention, therefore, blood is continually conducted through the blood processing system during both draw and return cycles. In an exemplary embodiment, the fraction by volume of the removed blood comprising the second portion is selected to prevent contamination of the collected non-red blood cell blood component(s) with red blood cells. In an embodiment providing high purities of collect components, recirculation of the recirculated portion maintains quasi-steady state flow conditions in the blood process system during removal and return cycles. In a preferred embodiment, recirculation of the recirculated portion maintains quasi-state state flow conditions in the blood processing system constant to within about 10%. Recirculation of a recirculated component in a manner maintaining quasi-steady state flow conditions in the blood system is beneficial because it provides more effective separation of blood components in blood processing systems, particularly blood processing systems employing a combination of density centrifugation and centrifugal elutriation separation methods. In addition, recirculation of a recirculated component is also beneficial because it provides for repeated processing of a portion of the removed blood, resulting in higher yields of collect components, such as white blood cells, plasma and platelets. This aspect of the present invention increases overall collection efficiency during blood processing.

In an embodiment of the present invention providing efficient separation and collection of plasma, platelets, white blood cells or any combination of these, the fraction by volume of the first portion of removed blood or anticoagulant-treated removed blood corresponding to collect components ($F_{cmax}$) is selected to prevent contamination of the collected blood components, particularly white blood cells, platelets and plasma, with red blood cells. Specifically, the portion of removed blood or anticoagulant-treated removed blood corresponding to collect components is selected to account for the enhanced hematocrit of the recirculated return component. As the fraction by volume of the removed blood corresponding to the collected component determines the hematocrt of the recirculated component due to mass balance, selection of the fraction by volume of the removed blood corresponding to the collected components may be used to ensure that the recirculation of hematocrit enhanced recirculated blood does not adversely affect blood processing. In the absence of a correction for the increased hematocrit of the recirculated component, spillover may occur when the average hematocrit of blood conducted through the blood processing system is significantly larger than the hematocrit of the donor/patient or the hematocrit of the anticoagulant-treated blood of the patient/donor. During spillover, the position of boundary layers between separated blood components in the blood processing system, such as a density centrifuge, are such that unwanted red blood cells are collected with other collected blood components, such as white blood cells, plasma, platelets or combinations of these. In one embodiment, $F_{cmax}$ is functionally related to the hematocrit of the recirculated component ($H_{recir}$). For example, $F_{cmax}$ may be a function of $H_{rem}/H_{recir}$, wherein $H_{rem}$ is the hematocrit of the removed blood or the anticoagulant-treated removed blood, such that the larger $H_{rem}/H_{recir}$ values result in smaller values of $F_{cmax}$. In another embodiment, $F_{cmax}$ is a variable of the duty cycle (D) of the blood processing system, the ratio of the blood flows through the blood processing system during draw and return cycles, the volume of removed blood or anti coagulant treated removed blood required to fill the return reservoir and the volume of the recirculated component or any combination of these variables. For example, $F_{cmax}$ may be a function of duty cycle such that smaller duty cycle values correspond to smaller values of $F_{cmax}$ and higher duty cycle values correspond to larger values of $F_{cmax}$. This functional dependence arises largely from the fact that less recirculated component having an enhanced hematocrit is recirculated through the blood processing system when the duty cycle is high and more recirculated component having an enhanced hematocrit is recirculated through the blood processing system when the duty cycle is low.

The methods and devices of the present invention are ideally suited for use in apheresis blood processing systems. For example, methods and devices of the present invention may be used for automated blood donation techniques for the collection of plasma, red blood cells, white blood cells, platelets or any combination of these blood components. In addition, the present methods may be used for therapeutic apheresis techniques and cell therapies, such as plasma exchange, red blood cell exchange or depletion, lymphoplasma exchange, immumospuresson therapies, and bone marrow processing. The selection of removal and return flow rates based on total blood volume, the use of time varying return flow rates or both substantially reduces the incidence of vein infiltration, hematoma and donor discomfort during apheresis blood processing. Furthermore, these aspects of the present invention also increase the efficiency of apheresis procedures by decreasing the incidence of vein collapse, vein blow out and access needle dislocation, which may reduce removal and return flows, require more frequent operator intervention and cause associated blood processing delays. Finally, recirculation of a return component and selection of $F_{collect}$ to prevent contamination of the collected blood components by red blood cells enhance the purity of plasma, white blood cells and platelets collected by apheresis methods and optimize collection efficiencies. The methods and devices of the present invention may be incorporated into commercially available apheresis systems such as the COBE Spectra® or TRIMA® apheresis systems, available from Gambro BCT, Lakewood, Colo., USA, or may be incorporated into apheresis systems and blood processing systems as described in U.S. Pat. Nos. 5,653,887, 6,053,856, 5,913,768, 6,674,173, 6,613,009 and 5,906,570.

The blood processing methods and devices of the present invention are particularly well suited for use with a single needle patient or donor access configurations. Use of a single needle access configuration is preferred for many applications because it involves only one blood removal and return interface established between the patient or donor and the outside environment and, therefore, substantially enhances patient or donor comfort during blood processing. An embodiment of the present methods using a single needle access configuration comprises the steps of removing blood at a rate proportional to a patient or donor's total blood volume for a removal time during a draw cycle. The removed blood is processed in a manner generating at least one return component, which is optionally accumulated in a fixed volume or variable volume return reservoir. At least a fraction by volume of the return component is returned to the subject at a return flow rate over a return time during a return cycle. Draw and return cycles are sequentially repeated during a selected blood processing time, whereby blood and/or blood components are cyclically removed from a subject, cyclically accumulated in the reservoir and cyclically pumped back to the subject. Removal and return flow rates based on total blood volume and ramped return flow rates or both are beneficial in blood processing systems having a single needle access system because these techniques substantially reduce access blood vessel infiltration and enhanced donor or patient comfort. In addition, methods of the present invention having $F_{collect}$ selected to prevent spillover and red blood cell contamination of collected non-red blood cell blood components are also of particular value to blood processing methods and devices employing a single access needle configuration.

The present methods and devices are also applicable to methods and devices utilizing a dual needle access configuration. Application of the methods of the present invention to dual needle access configurations involve continuous removal and return flows which are directed through first and second access needles, respectively.

In one embodiment of the present invention utilizing a dual needle access configuration, removal and return flow rates are selected on the basis of total blood volume. Removal and return flow rates in dual needle systems are typically dependent on each other to maintain mass balance of removed blood, collected blood components and returned blood components.

The methods and devices of the present invention may be broadly applied to the infusion of any material into an access blood vessel or the removal of any material from an access blood vessel. Specifically, methods of removing biological fluids employing removal flow rates based on total blood volume and removal flow rates which vary systemically as a function of time may be applied to other treatment procedures such as blood dialysis peritoneal dialysis, hemodialysis and immunosuppression therapies. In addition, methods of the present invention providing for a reduction of incidence of blood vessel infiltration, patient discomfort and access needle dislocation may be useful for administering fluids intravenously, such as medicines, biological materials and nutrients. For example, infusion rates based on total blood volume and infusion rates which vary systemically with time may be useful in a variety of drug therapies including, but not limited to, pain management, chemotherapy, administration of antibiotics, parenteral nutrition, HIV related therapies, administration of hemophilia factor and human growth hormone, biological response modification, and the administration of aerosolized medications.

In another aspect the present invention provides methods of reducing the incidence of vein infiltration during blood processing. An exemplary method of this aspect of the present invention comprises the steps of: (1) removing blood from a subject for a removal time at a removal flow rate, thereby generating removed blood; (2) processing said removed blood, thereby generating processed blood including at least one return component; (3) returning at least a portion of said return component to said subject over a return time at a return flow rate; and (4) systematically varying said return flow rate over said return time. An another exemplary method of this aspect of the present invention comprises the steps of: (1) determining the total blood volume of a subject undergoing a blood processing procedure; (2) removing blood from said subject at a selected removal flow rate thereby generating removed blood, wherein said selected removal flow rate is derived from said total blood volume; (3) processing said removed blood, thereby generating processed blood including at least one return component; and (4) returning at least a portion of said return component to said subject at a selected return flow rate, wherein said selected return flow rate is derived from said total blood volume of said subject.

The invention is further illustrated by the following description, examples, drawings and claims.

DETAILED DESCRIPTION OF THE INVENTION

Figure 1:
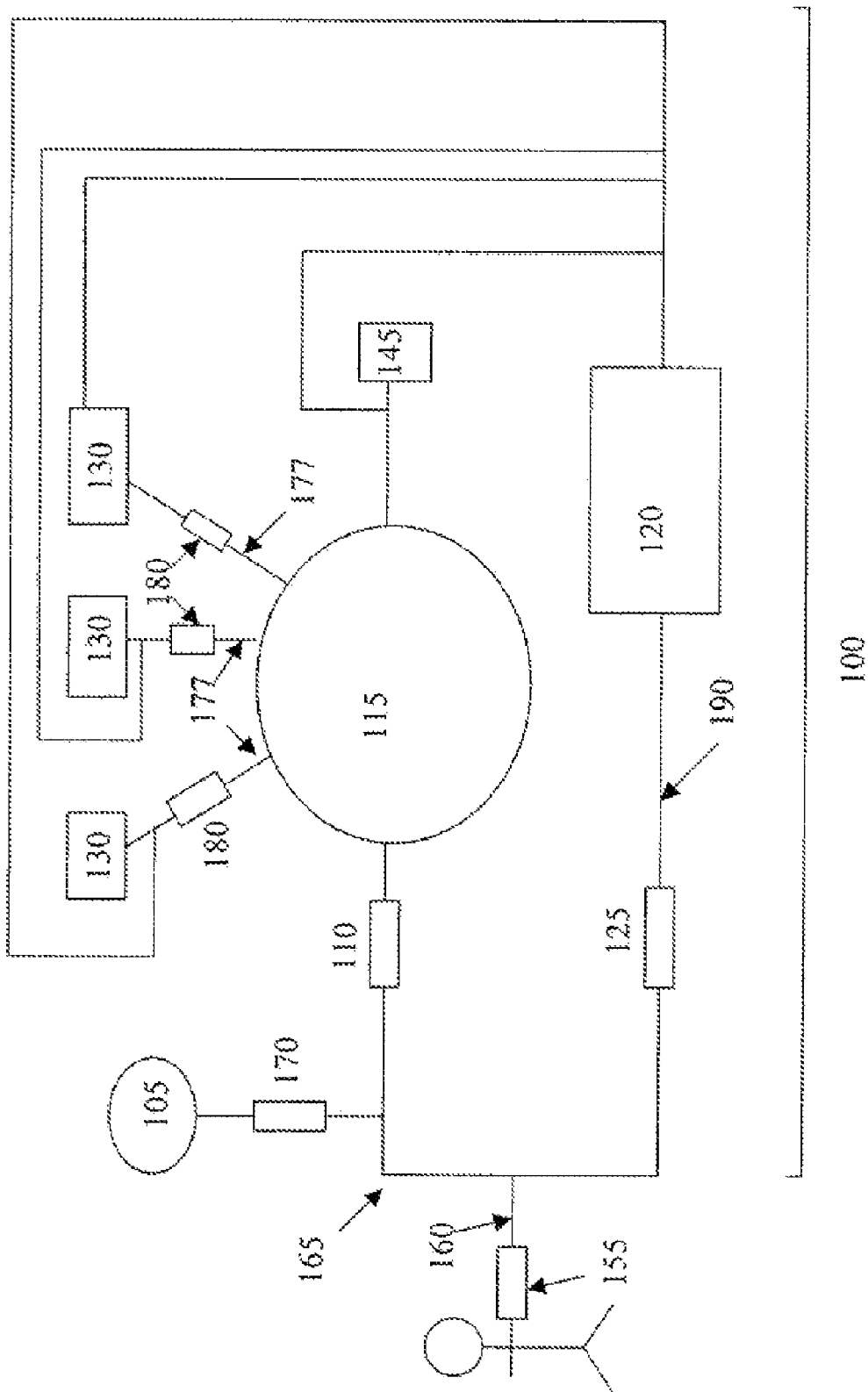
FIG. 1 is a schematic drawing showing an exemplary blood processing system of the present invention FIG. 2A provides plots of the ratio of the return flow rate to average flow rate as a function of the fraction of return time ($t/t_r$). Line (A) corresponds to $F_0$ equal to 0.5, line (B) corresponds to $F_0$ equal to 1 and line (C) corresponds to $F_0$ equal to 1.5.

Referring to the drawings, like numerals indicate like elements and the same number appearing in more than one drawing refers to the same element. In addition, hereinafter, the following definitions apply:

"Blood processing" refers to the manipulation of a blood sample or component thereof, to realize a change in composition. Blood processing includes methods of separating blood or a component thereof into blood components or subcomponents, methods of collecting separated blood components or subcomponents, methods of removing blood components and/or removed blood, methods of infusing blood or blood components into a patient or donor, leukoreduction, pathogen inactivation, pathogen removal, blood component washing, red blood cell deglycerolization, or any combination of these processes. The present invention provides improved methods of blood processing wherein blood or blood components thereof are separated into components or subcomponents on the basis of density, size, shape, mobility, diffusion rate, sedimentation velocity, surface chemistry properties or combinations of these characteristics.

"Blood," "blood product" and "blood component" as used herein include whole blood samples, blood components and blood products which may be derived from whole blood or a component thereof. "Blood," "blood product" and "blood component" as used herein also include anticoagulant-treated blood, anticoagulant-treated blood components and anticoagulant-treated blood products. Cellular blood components include, but are not limited to erythrocytes (red blood cells), leukocytes (white blood cells), esinophils, monocytes, lymphocytes, granulacytes, basophils, plasma, and blood stems cells. Non-cellular blood components include thrombocytes (platelets), plasma, and blood proteins isolated from blood samples including, but not limited to, factor III, Von Willebrand factor, factor IX, factor X, factor XI, Hageman factor, prothrombin, anti-thrombin III, fibronectin, plasminogen, plasma protein fraction, immune serum globulin, modified immune globulin, albumin, plasma growth hormone, somatomedin, plasminogen, streptokinase complex, ceruloplasmin, transferrin, haptoglobin, antitrypsin and prekallikrein.

"Fluid" refers to any material which is capable of conforming to the shape of the container in which it is held. Fluids useable with methods of the present invention include, but are not limited to, colloids, liquids, bodily fluids, such as blood and blood components and subcomponents, intravenous medicines and intravenous nutrients.

"Access blood vessel" refers to one or more blood vessels which conduct blood or blood components out of a patient or donor, conduct blood or blood components into a patient or donor or both. Preferred access blood vessels in the present invention are veins. Other access blood vessel useable in the methods of the present invention include arteries, capillaries, venules, and arterioles.

"Hematocrit" refers to the volume of blood occupied by red blood cells (erythrocytes) relative to the total volume of a blood sample or a blood component sample. Hematocrit (H) is typically expressed as a percentage and defined by the equation:

$$H = 100 \times \left( \frac{V_{rbc}}{V_{sample}} \right); \tag{1}$$

wherein $V_{rbc}$ is the volume of red blood cells and $V_{sample}$ is the volume of a sample, which may be whole blood, processed blood, one or more separated blood components or more processed blood components, a collect component, a recirculated component, a return component or any combination of these.

"Substantially linear manner" refers to changes of one or more variables which may be represented by a linear relationship. Variation of a parameter in a substantially linear manner is intended to include some amount of deviation from absolute linear variation. In a preferred embodiment, variation of a parameter in a substantially linear manner includes deviations from absolute linearity less than 10%, over the relevant range of values. In a more preferred embodiment, variation of a parameter in a substantially linear manner includes deviations from absolute linearity less than 5%, over the relevant range of values. In the present invention, return flow rates may be varied in a substantially linear manner during return cycles, preferably decreased in a substantially linear manner.

"Collect component" refers to a portion of removed blood or anticoagulant-treated removed blood which is collected. In an exemplary embodiment of the present invention, collect components are blood components, preferably substantially purified blood components. Collect components may be generated by any blood processing means including but not limited to, density centrifugation, centrifugal elutriation, size and shape filtration, affinity chromatography or any combination of these techniques. Collect components of the present invention may be characterized in terms of their fraction by volume, which refers to the fraction of removed blood or anti coagulant treated removed blood comprising one or more collect components. Collect components may be used as therapeutic agents in infusion medicine, stored for future use or returned to a patient in a therapy.

"Return component" refers to a portion of removed blood or anticoagulant-treated removed blood which is returned to the subject of a blood processing procedure. Return components may comprise whole blood or one or more blood components. In some blood processing procedures, such as apheresis procedures, the return component is characterized by a hematocrit which is different from the hematocrit of the removed blood or anticoagulant-treated removed blood. In an exemplary embodiment of the present invention, return components are returned to a patient or donor during the return time of a return cycle. In an exemplary embodiment of the present invention providing reduced risk of access capillary infiltration and optimized donor or patient comfort, the return flow rate of return components is derived from a subject's total blood volume and is controlled such that it decreases systematically during the return time.

"Recirculated component" refers to a portion of removed blood or anticoagulant-treated removed blood, which is recirculated through a blood separation system during blood processing. In an embodiment of the present invention, recirculation of a recirculated component through a blood separation system maintains quasi-steady state flow conditions in the blood processing system. In blood processing procedures involving the collection of blood components, the recirculated component may have a hematocrit that is different from the hematocrit of the removed blood or anticoagulant-treated removed blood. In blood processing procedures involving the collection of plasma, white blood cell or platelet components, for example, the hematocrit of the recirculated component may be larger than the hematocrit of the removed blood or anticoagulant-treated removed blood.

"Substantially exponential manner" refers to changes of one or more variables which may be accurately represented by an exponential relationship. Variation of a parameter in a substantially exponential manner is intended to include some amount of deviation from absolute exponential variation. In a preferred embodiment, variation of a parameter in a substantially exponential manner includes deviations from purely exponential behavior less than 10%, over the relevant range of values. In a more preferred embodiment, variation of a parameter in a substantially exponential manner includes deviations from purely exponential behavior less than 5%, over the relevant range of values. In the present invention, return flow rates may be varied in a substantially exponential manner during return cycles, preferably decreased in a substantially exponential manner.

"Substantially logarithmic manner" refers to changes of one or more variables which may be accurately represented by a logarithmic relationship. Variation of a parameter in a substantially logarithmic manner is intended to include some amount of deviation from absolute logarithmic variation. In a preferred embodiment, variation of a parameter in a substantially logarithmic manner includes deviations from purely logarithmic behavior less than 10%, over the relevant range of values. In a more preferred embodiment, variation of a parameter in a substantially logarithmic manner includes deviations from purely logarithmic behavior less than 5%, over the relevant range of values. In the present invention, return flow rates may be varied in a substantially logarithmic manner during return cycles, preferably decreased in a substantially logarithmic manner.

"Substantially quadratic manner" refers to changes of one or more variables which may be accurately represented by a quadratic relationship. Variation of a parameter in a substantially quadratic manner is intended to include some amount of deviation from absolute quadratic variation. In a preferred embodiment, variation of a parameter in a substantially quadratic manner includes deviations from purely quadratic behavior less than 10%, over the relevant range of values. In a more preferred embodiment, variation of a parameter in a substantially quadratic manner includes deviations from purely quadratic behavior less than 5%, over the relevant range of values. In the present invention, return flow rates may be varied in a substantially quadratic manner during return cycles, preferably decreased in a substantially quadratic manner.

"Efficient blood component collection" refers to collection of substantial amounts of one or more selected blood components, such as white blood cells, red blood cells, plasma, platelets, and blood proteins during a selected blood processing time. Efficient blood component collection provides high yields and high purities of blood components collected over short blood processing times. Methods of the present invention enhance the efficiency of blood component collection with respect to conventional methods.

"Systematically varying" refers to a process whereby a parameter is changed or manipulated in a controlled manner. In the present invention, parameters such as return flow rate, removal flow rate, return time, removal time, the fraction of removed blood collected or recirculated may be systematically varied by substantially linear variations, exponential variations, logarithmic variations, quadratic variations. Exemplary blood processing methods of the present invention having selected return flow rates which are varied systematically over a return time decrease the incidence of blood vessel infiltration and donor or patient discomfort.

"Access needle" refers to a device or device component operationally connected to an access blood vessel for establishing fluid interconnection between a subject and an extracorporeal environment, such as a blood processing system. Access needles of the present invention are used for removing fluids, returning fluids or both to a patient or donor. Access needles of the present invention may be any device or device component capable of establishing fluid interconnectivity between a subject and an extracorporeal environment. An exemplary access needle useable in the present invention comprises device or device component having a central axial bore capable of conducting blood and blood components into and/or out of a patient or donor. Access needles useable in the present invention may be utilized in both single and dual needle access configurations.

"Duty cycle" refers to a parameter which characterizes the amount of time blood is removed from a subject relative to the amount of time blood or blood components are returned to a subject during blood processing. In an exemplary embodiment, duty cycle (D) is related to the amount of time blood is removed from a patient or donor blood during a draw cycle ($t_{rem}$) and to the amount of time blood or blood components are returned to a patient or donor blood during a return cycle ($t_{ret}$) by the expression:

$$D = \frac{t_{rem}}{(t_{rem} + t_{ret})}; \quad (2)$$

The present invention includes methods of processing blood wherein the fraction of removed blood corresponding to one or more collected components is a function of duty cycle.

"Fraction by volume of the removed blood corresponding to the collected component" refers to the fraction by volume of the removed blood and/or anticoagulant-treated removed blood which is collected during blood processing and is designated by the variable $F_{cmax}$. This fraction may correspond to a single collected component or a plurality of collected components. In an exemplary embodiment, the fraction by volume of the removed blood corresponding to the collected component is defined by the equation:

$$F_{cmax} = \left(\frac{V_{col}}{V_{total}}\right); \quad (3)$$

wherein $V_{col}$ is the volume of one or more collected components and $V_{total}$ is the total volume of the removed blood or the anticoagulant-treated removed blood. $F_{cmax}$ may be defined with respect to a variety of time intervals including: the total blood processing time or a time interval corresponding to a selected collection procedure, such as a plasma collect procedure, a platelet and white blood cell collect procedure, or a red blood cell collect procedure. In addition, $F_{cmax}$ may be defined with respect to the removal cycle, return cycle or the summation of return and removal cycles.

"Single needle access configuration" refers to an arrangement for removing bodily fluids from a subject, returning at least a portion of a return component or both. A single needle access configuration is characterized by the presence of one access needle for conducting fluids, such as blood or blood components, to and from a patient or donor. Blood processing methods and devises employing a single needle configuration are preferred for some blood processing applications because it involves a single blood removal and return interface established between the patient or donor and the outside environment and, therefore, substantially enhances patient or donor comfort during blood processing.

"Dual access needle configuration" refers to an arrangement for removing bodily fluids from a subject and returning at least a portion of a return component. A dual needle access configuration is characterized by the presence two fluid interconnections: (1) a first access needle for conducting fluids, such as blood or blood components, from a patient or donor to a blood processing system and (2) a second access needle for conducting fluids, such as a return component or portion of removed blood into a patient or donor.

"Blood vessel infiltration" refers to damage to the walls of a blood vessel, such as an access blood vessel. In some contexts, infiltration relates perforation of the walls of blood vessel, such as an access vein, which may cause blood to infiltrate surrounding tissue. Infiltration may be caused by an increase or decrease in pressure in an access blood vessel, vein blow out, vein collapse, access needle movement and/or dislocation, removal of blood or blood components from a subject undergoing blood processing, return of blood or blood components to a subject undergoing blood processing, or any combination of these.

In the following description, numerous specific details of the devices, device components and methods of the present invention are set forth in order to provide a thorough explanation of the precise nature of the invention. It will be apparent, however, to those of skill in the art that the invention can be practiced without these specific details.

This invention provides methods, devices and device components for processing biological fluids, preferably blood and blood components. In particular, the present invention provides methods and devices for separating blood into blood components and collecting purified, separated blood components, which are useful for reducing the incidence of infiltration of an access blood vessel and increasing donor or patient comfort during blood processing. Further, the present blood processing methods and devices provide improved collection efficiency and enhanced purities of collected blood components relative to conventional methods.

FIG. 1 schematically illustrates an exemplary embodiment of the blood processing methods and devices of the present invention utilizing a single access needle configuration. The illustrated blood processing system 100 comprises anticoagulant reservoir 105, inlet pump 110, blood separation system 115, return reservoir 120 and return pump 125. Optionally, blood processing system 100 may further comprise one or more collection reservoirs 130, such as a white blood cell collection reservoir, a platelet collection reservoir, a plasma collection reservoir and/or a red blood cell collection reservoir. Blood processing system 100 is in fluid communication with a subject 150 via donor access line 160 and access needle 155, which is operationally connected to an access blood vessel, such as a vein.

To achieve blood processing, blood is removed from subject 150 through access needle 155 at a removal flow rate during a draw cycle. The removed blood flows through donor access line 160 which is in fluid connection with access needle 155 and inlet line 165. The removed blood is treated with an anticoagulant agent pumped into the inlet line 165 from anticoagulant reservoir 105 via an anticoagulant pump 170. Anticoagulant-treated blood is conducted through blood separation system 115 by inlet pump 110, wherein its is separated into a plurality of discrete blood components on the basis of on the basis of shape, size, sedimentation velocity, diffusion rate, surface chemistry characteristics or any combination of these properties. Separation of anticoagulant-treated removed blood in blood separation system 115 generates at least one collect component. One or more portions of the anticoagulant-treated removed blood corresponding to collect components are conducted out of blood separation system 115 through collect lines 177 into one or more physically separated collection reservoirs 130 via one or more collection pumps 180. The remainder of the anticoagulant-treated removed blood is flowed out of blood separation system 115 into return reservoir 120, preferably a fixed volume reservoir. The remainder of the anticoagulant-treated blood accumulates in return reservoir 120 during the draw cycle until achieving a selected volume, wherein a return cycle is triggered. During the return cycle, the accumulated anticoagulant-treated blood is pumped out of the return reservoir 120 into return line 190 by return pump 125. A portion the anticoagulant-treated removed blood corresponding to a recirculated component is recirculated through blood separation system 115. Another portion the anticoagulant-treated removed blood corresponding to a return component is returned to the subject 150 at a return flow rate through the donor access line 160 and the access needle 155.

In an exemplary embodiment, draw and return cycles are sequentially repeated for a selected blood processing time. In this manner, blood and/or blood components are cyclically removed from the subject, cyclically accumulated in the reservoir and cyclically pumped back to the subject. In an exemplary embodiment, draw and return cycles are sequentially repeated to achieve a selected extent and duration of blood processing or to accumulate a selected amount of one or more collect components. Individual separated blood components or a plurality of selected components are collected during both draw and return cycles. In a preferred embodiment, a plurality of selected blood components are simultaneously collected. Alternatively, individual blood components may be collected sequentially at different collection times in a blood processing procedure. Recirculation of a portion of the anticoagulant-treated removed blood corresponding to a recirculated component is beneficial in the present invention because it ensures that quasi-steady state flow conditions are maintained in the separation system 115 and collect lines 177 which provides for efficient collection of purified blood components, such as white blood cells, plasma and platelets. In an embodiment providing high purities of collected components, the rate, volume or both of the flow of recirculated component is selected such that quasi-steady state flow conditions in the blood separation system 115 and collect lines 177 are constant to within approximately 10%. This attribute of the present invention is particularly beneficial for embodiments having a blood processing separation system comprising a density centrifuge and a centrifugal elutriation system.

In an exemplary embodiment, blood separation system 115 is a density centrifuge in fluid communication with a centrifugal elutriation system. In this embodiment, anticoagulant-treated removed blood is first conducted from inlet line 165 through a density centrifuge, wherein blood components are separated on the basis of density. Specifically, the centrifugal field generated in the density centrifuge separates the anticoagulant-treated blood into a higher density fraction primarily comprising red blood cells and a lower density fraction primarily comprising plasma. In addition, an intermediate density fraction comprising platelets and leukocytes forms an interface layer between the higher and lower density fractions. Separated fractions corresponding to collect components are withdrawn through separate exit ports. These fractions may be collected or subjected to further fractionation. For example, the intermediate density fraction comprising platelets and white blood cells may be subjected to further processing via centrifugal elutriation. In an exemplary embodiment, the intermediate density fraction is introduced into a flow of liquid elutriation buffer and passed into a funnel-shaped separation chamber located in the spinning centrifuge. As the liquid buffer flows through the separation chamber, the liquid sweeps smaller sized, slower sedimenting cells toward an elutriation boundary within the chamber. Larger, faster-sedimenting cells, however, migrate toward an area of the chamber having the greatest centrifugal force. By selecting the proper fluid flow rates through the funnel-shaped separation chamber, faster sedimenting cells and slower-sedimenting cells may be separately extracted from the separation chamber and subsequently collected. In this manner, white blood cells and platelets may be separated and subsequently collected in separate collect reservoirs. Therefore, the combination of density centrifugation and centrifugal elutriation provides methods of separating blood components based on both density and sedimentation velocity properties.

In exemplary blood processing methods of the present invention, the return flow rate of returned blood components through access needle 155 is systematically decreased for a return time during the removal cycle. In this embodiment of the present invention, the return flow rate is set at an initial maximum return flow rate at the onset of the return cycle. The return flow rate is systematically decreased by adjusting the pumping rate of return pump 125 during the return cycle. At the end of the return cycle, the flow of blood and blood components through access needle 155 changes direction and the adjacent draw cycle is initiated. This controlled flow behavior continues for repeated return and draw cycles during a selected blood processing time.

In another embodiment of the present invention, the return flow rate is varied linearly during each return cycle. For example, return flow rates in the present invention may be provided by the equation:

$$Z_{ret}=[F_0+2(1-F_0)(t/t_r)]Q_{ret}; \qquad (4)$$

wherein $Z_{ret}$ is said return flow rate, t is time, $F_0$ has a value greater than or equal to 0 and less than or equal to 2, $t_r$ is the return time and $Q_{ret}$ is the average return flow rate. In the context of this embodiment, average return flow rate ($Q_{ret}$) in Equation 4 corresponds to the value of $Z_{ret}$ for $F_0$ equal to 1. In an exemplary embodiment, the initial return flow rate is set to a value such that less than 0.1% hemolysis occurs during blood processing, preferably a value selected from the range of about 50 ml min$^{-1}$ to about 400 ml min$^{-1}$ and more preferably a value of about 300 ml min$^{-1}$. The parameter $F_0$ in Equation 4 determines the direction in which the return flow rate changes with respect to time, wherein a value of $F_0$ less than 1 corresponds to an increasing return flow rate during the return cycle and a value of $F_0$ greater than 1 corresponds to a decreasing return flow rate during the return cycle. $F_0$ also establishes the rate of change of the return flow rate. In a preferred embodiment of the present invention providing reduced access blood vessel infiltration and enhanced donor comfort, $F_0$ is greater than 1 and less than or equal to 2.

Figure 2A:
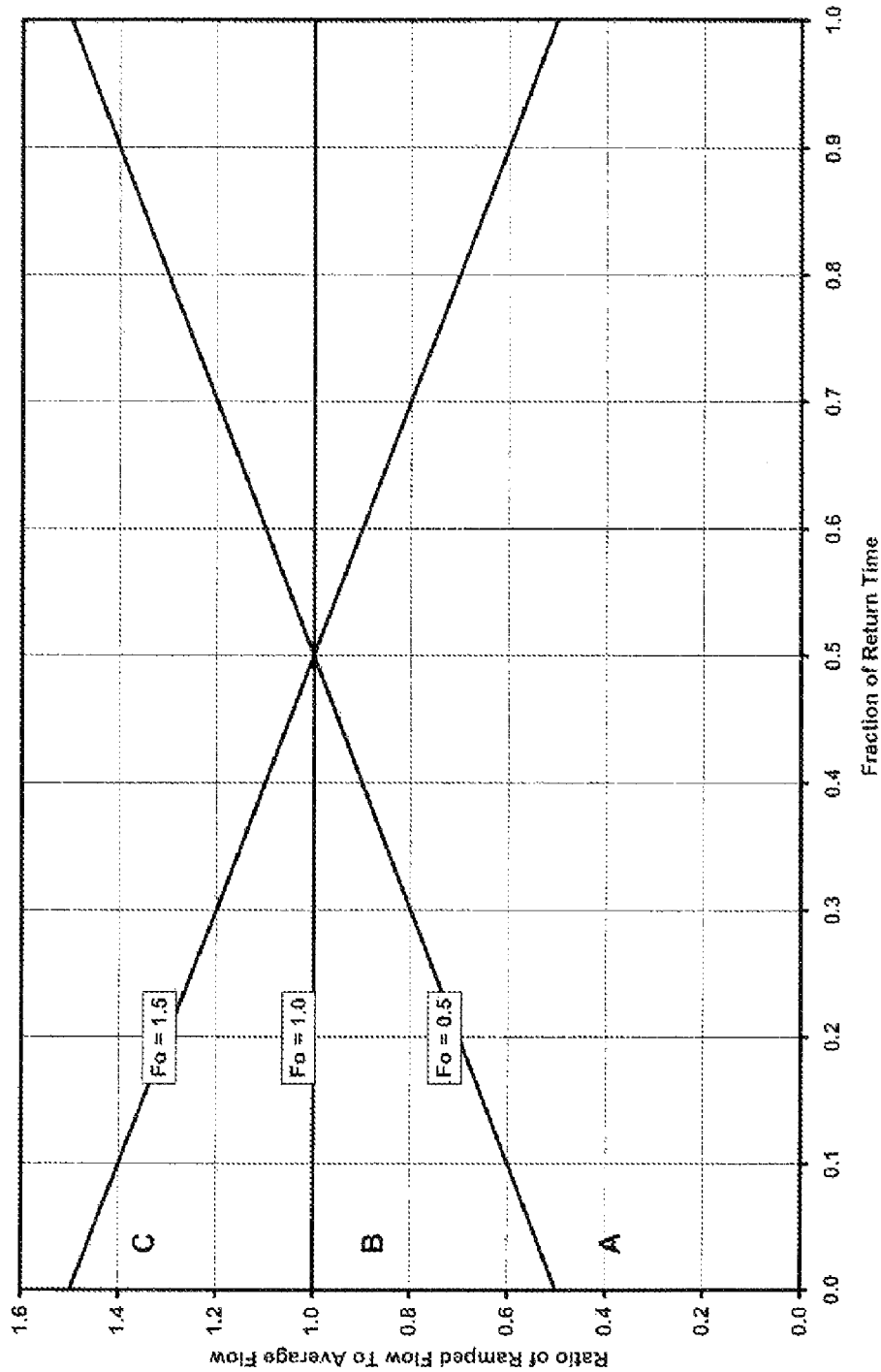
FIG. 2B is a plot showing the fraction of the return component volume returned to the subject as a function of the fraction of the return time ($t/t_r$) for $F_0$ equal to 0.5 (A), 1 (B) and 1.5 (C).
FIG. 2C is a plot of the calculated change in vein pressure ($\Delta p$) as a function of the fraction of the return time ($t/t_r$) for $F_0$ equal to 0.5 (A), 1 (B) and 1.5 (C).
FIG. 2D provides a plot of the ratio of the change in vein pressure at the end of a 20 second return cycle and the change in pressure at the end of a 20 second return cycle for $F_0$ equal to 1 as a function of $F_0$.
Figure 2B:
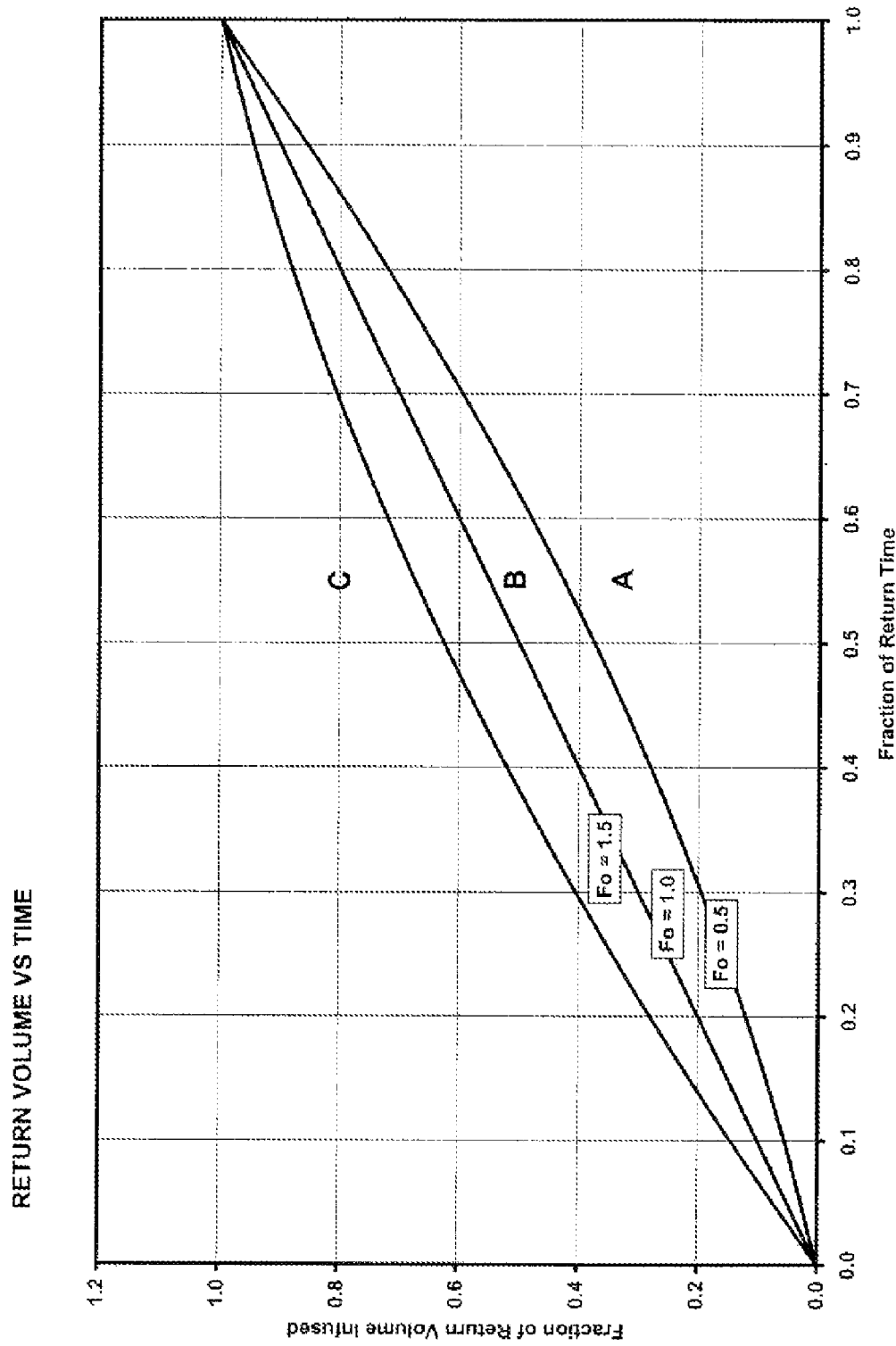

FIG. 2A provides a graphical representation of Equation 4, wherein the ratio of the return flow rate ($Z_{ret}$) to the average return flow rate is plotted as a function of the fraction of the return time (t/$t_r$). In FIG. 2A, line (A) corresponds to $F_0$ equal to 0.5, line (B) corresponds to $F_0$ equal to 1 and line (C) corresponds to $F_0$ equal to 1.5. FIG. 2B is a plot showing the fraction of the return component volume returned to the subject as a function of the fraction of the return time (t/$t_r$) for $F_0$ equal to 0.5 (A), 1 (B) and 1.5 (C). While the same net volume of return component is returned during the return cycle for each value of $F_0$, the temporal profiles of the returned volumes differ substantially.

Figure 2C:
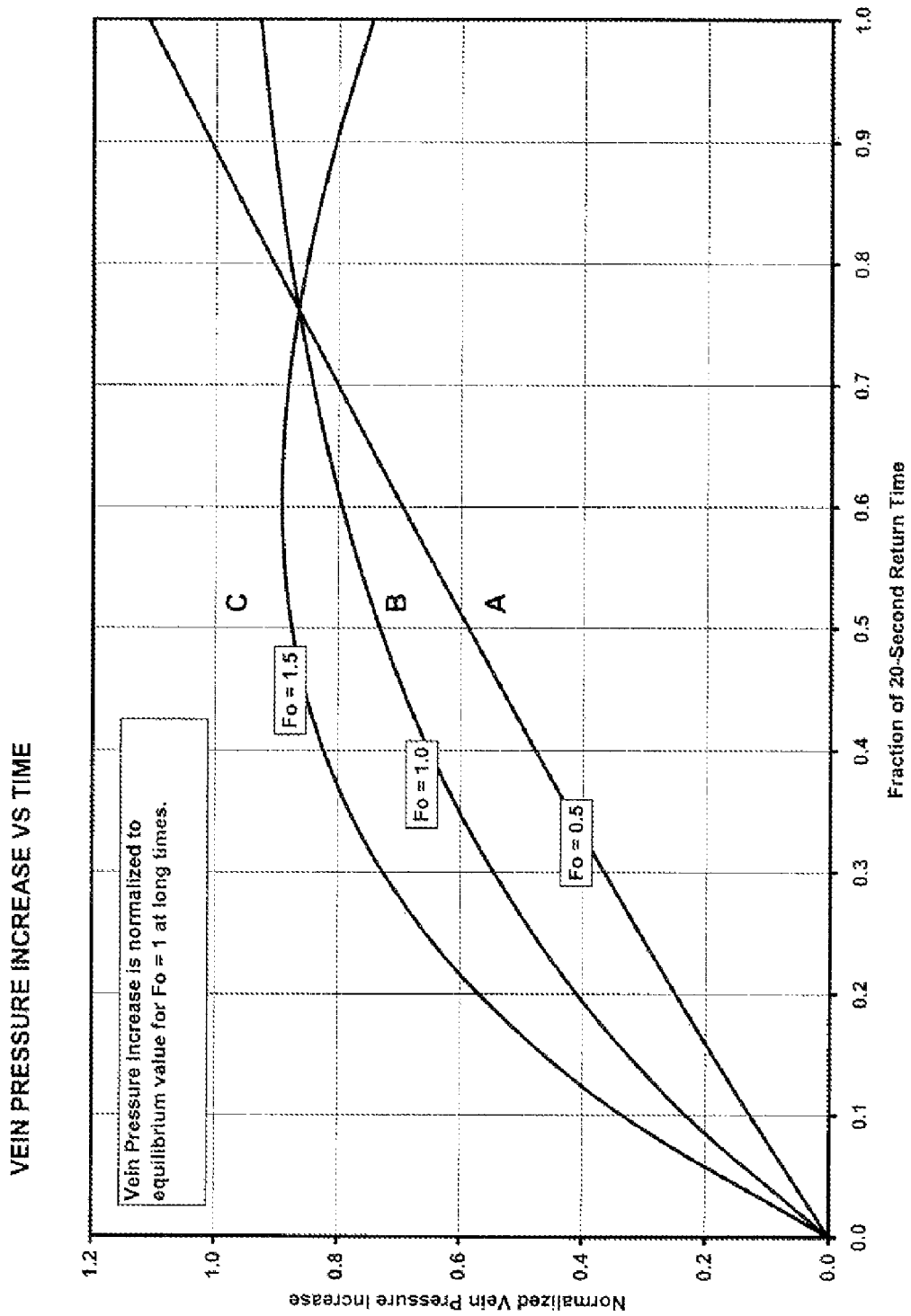
Figure 2D:
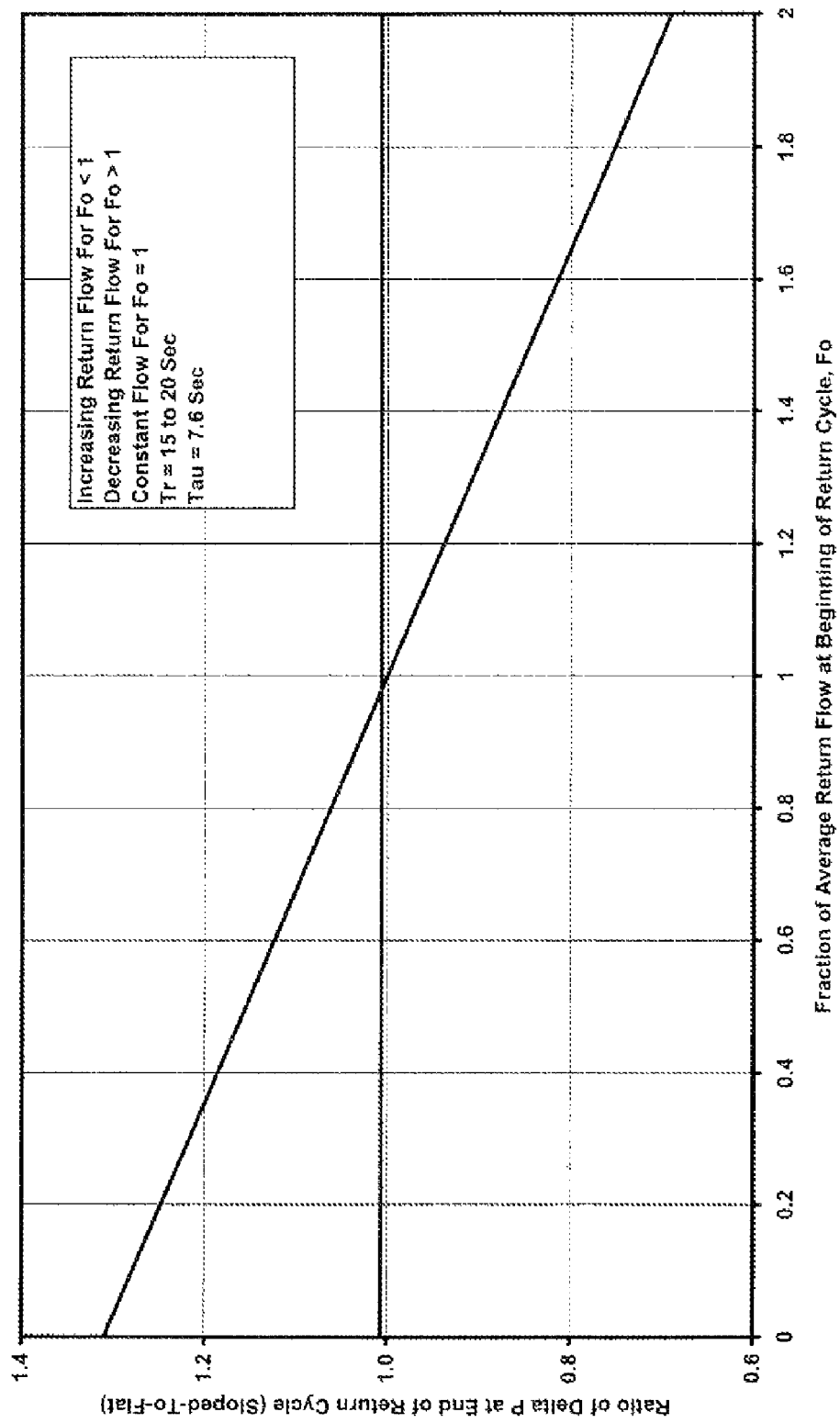

As a consequence of this different temporal behavior, access veins accommodating the return volume are expected to undergo different expansion dynamics resulting from return component flows. To evaluate the effects of different return flow rate temporal profiles on vein expansion dynamics, vein pressure temporal profiles for each return flow rate profile illustrated in FIG. 2A were calculated for a 20 second return time ($t_r$). FIG. 2C is a plot of the calculated change in vein pressure (Δp) as a function of the fraction of the return time (t/$t_r$) for $F_0$ equal to 0.5 (A), 1 (B) and 1.5 (C). As shown in FIG. 2C, selection of a value of $F_0$ equal to 1.5 results in the smallest net change in vein pressure and results in the smallest vein pressure increase at the end of the 20 second return time interval. These effects largely result from a return flow rate profile, wherein smaller volumes of return component are conducted into the vein when it is at is largest expansion states. FIG. 2D provides a plot of the ratio of the change in vein pressure at the end of a 20 second return cycle and the change in pressure at the end of a 20 second return cycle for $F_0$ equal to 1 as a function of $F_0$. As shown in FIG. 2D, use of return flow rates which decrease linearly as a function of time results in lower vein pressures at the end of the return cycle.

The lower increases in vein pressure associated with return flow rates which decrease linearly as a function of time ($F_0 > 1$), as illustrated in FIGS. 2C and 2D, are expect to have beneficial consequences with respect to blood processing. First, lower net changes in vein pressure during blood processing decrease the risk of vein infiltration and hematoma. Vein infiltration and hematoma result in processing delays or termination of a blood processing procedure and, therefore, may substantially affect the duration and efficiency of blood processing. Second, lower net changes in vein pressure substantially enhance donor or patient comfort during blood processing. This may result in better patient satisfaction and donors which donate blood or blood components more frequently. Finally, lower net changes in vein pressure during blood processing decrease the risk of access needle dislocation cause by pressure fluctuations. Minimizing changes in needle position is beneficial for avoiding unwanted removal flow rate and/or return flow rate decreases, which may cause delays in blood processing and require greater operator or physician intervention.

In another exemplary embodiment, the present invention provides blood processing methods and devices having return flow rates, removal flow rates or both which are derived from a subject's total blood volume. Exemplary return flow rates and removal flow rates employed in the methods of the present invention are positively correlated to total blood volume, wherein larger return flow rates, removal flow rates or both are employed for subjects having larger total blood volumes. In exemplary blood processing methods, a subject's total blood volume is determined and return flow rates, removal flow rates or both are established by a mathematical relationship relating one or both of these rates to total blood volume. Total blood volume may be determined by any means known in the art of physiology and anatomy. For example, total blood volume may be determined using correlations involving physiological characteristics of the subject, such as height, weight, gender, age and ethnicity. In an exemplary method of the present invention, total blood volume ($V_B$) is determined using a subject's length in centimeters (L) and weight in kilograms (W) by the equations:

$$V_B = 604 + (3.669 \times 10^{-4})(L^3) + (32.187)(W); \quad (5)$$

and $$V_B = 183 + (3.561 \times 10^{-4})(L^3) + (33.069)(W); \quad (6)$$

wherein Equation 5 corresponds to male subjects and Equation 6 corresponds to female subjects.

In an exemplary embodiment of the present invention, return flow rates, removal flow rates or both are determined by a linear relationship relating flow rate to total blood volume. For example, return and removal flow rates may be related to a subject's total blood volume by the following equations:

$$Z_{rem} = (C_{qi}) \times (A_{rem}) \times (V_B); \quad (7)$$

$$Z_{ret} = (C_{qr}) \times (A_{ret}) \times (V_B); \quad (8)$$

wherein $Z_{ret}$ is the return flow rate, $Z_{rem}$ is the removal flow rate, $V_B$ is total blood volume, $C_{qi}$ is a first selectably adjustable parameter, $C_{qr}$ is a second selectably adjustable parameter, $A_{ret}$ is a first constant and $A_{rem}$ is a second constant. In an exemplary embodiment, $A_{ret}$ is a value selected from the range of about 0.05 min$^{-1}$ to about 0.20 min$^{-1}$, preferably 0.075 min$^{-1}$, $A_{rem}$ is a value selected from the range of about 0.01 min$^{-1}$ to about 0.05 min$^{-1}$, preferably 0.030 min$^{-1}$. $C_{qi}$ and $C_{qr}$ are selectably adjustable variables which are selected on the basis of the comfort of the patient or donor. In an exemplary embodiment, $C_{qi}$ is a value selected from the range of about 0.66 to about 1.00 and $C_{qr}$ is a value selected from the range of about 0.5 to about 1.00. Equations 7 and 8 may optionally include maxima $Q_{rem\,max}$ and $Q_{ret\,max}$ as shown in Equations 9 and 10:

$$Z_{rem} = (C_{qi}) \times (A_{rem}) \times (V_B) \leq Q_{rem\,max}; \quad (9)$$

$$Z_{ret} = (C_{qr}) \times (A_{ret}) \times (V_B) \leq Q_{ret\,max}; \quad (10)$$

In an exemplary embodiment of the present invention, $Z_{ret}$ and $Z_{rem}$ are limits corresponding to maximum return flow rates and removal flow rates, respectively. In this embodiment, return flow rates and removal flow rates employed during processing are selected such that they are values less than $Z_{ret}$ and $Z_{rem}$.

As readily understood by persons of skill in the art of blood processing and fluid mechanics, it is difficult to control fluid flows, such as flows of blood and blood components to and from a subject undergoing a blood processing procedure, in a manner providing an absolute linear correlation between these flow rates and total blood volume. Accordingly, the present invention includes embodiments wherein deviations from absolute linearity, preferably deviation less than 10%, are observed. As will also be clear to one of ordinary skill in the art of extracorporeal blood processing, the methods of the present invention may be practiced using return flow rates, removal flow rates or both which are derived from total blood volume using non-linear functional relationships, such as exponential correlations, logarithmic correlations, quadratic correlations and combinations of these. In exemplary embodiments of the present invention employing non-linear correlations between removal flow rate and/or return flow rate and total blood volume, these rates are derived from functional relationships wherein the removal flow rate, return flow rate or both increase with increasing total blood volume of a patient or donor.

In another exemplary embodiment, $C_{qi}$ and $C_{qr}$ are correlated and have the values, as indicated in Table 1, which correspond to six operation levels available to an operator or physician conducting blood processing.

TABLE 1

Exemplary values of $C_{qi}$ and $C_{qr}$.

| Level | $C_{qi}$ | $C_{qr}$ |
|---|---|---|
| 1 | 0.66 | 0.50 |
| 2 | 0.72 | 0.57 |
| 3 | 0.78 | 0.66 |
| 4 | 0.85 | 0.76 |
| 5 | 0.92 | 0.87 |
| 6 | 1.00 | 1.00 |

Levels 1 through 6 indicated in Table 1, correspond to different degrees of blood processing aggressiveness, wherein level 1 corresponds to the lowest degree of aggressiveness and level 6 corresponds to the highest degree of aggressiveness. In the context of this description, aggressiveness in blood processing procedures relates to how rapidly a selected blood processing procedure is initiated, maintained and concluded. Selection of a lower operation level is beneficial in some applications because it results in enhanced donor comfort and decreases the incidence of access blood vessel infiltration. Selection of a higher operation level is beneficial in other applications because it results in greater blood processing efficiency and shortened net blood processing times. In an exemplary embodiment of the present invention, an operator or physician is able to adjust a blood processing system to select a desired blood processing operation level reflecting a desired extent of aggressiveness. Further, the present invention includes embodiments wherein an operator or physician is able to change the operation level selected during a blood processing procedure to maximize donor comfort, increase or decrease net blood processing time, reduce the risk of vein infiltration and/or hematoma or any combination of these functions. As readily understood by a person of skill in the art of extracorporeal blood processing and fluid dynamics, the present invention also includes embodiments having more than six blood processing operation levels. Embodiments having more than six operation levels is beneficial because it provides more flexible control of the aggressiveness of a selected blood processing procedure.

Figure 3A:
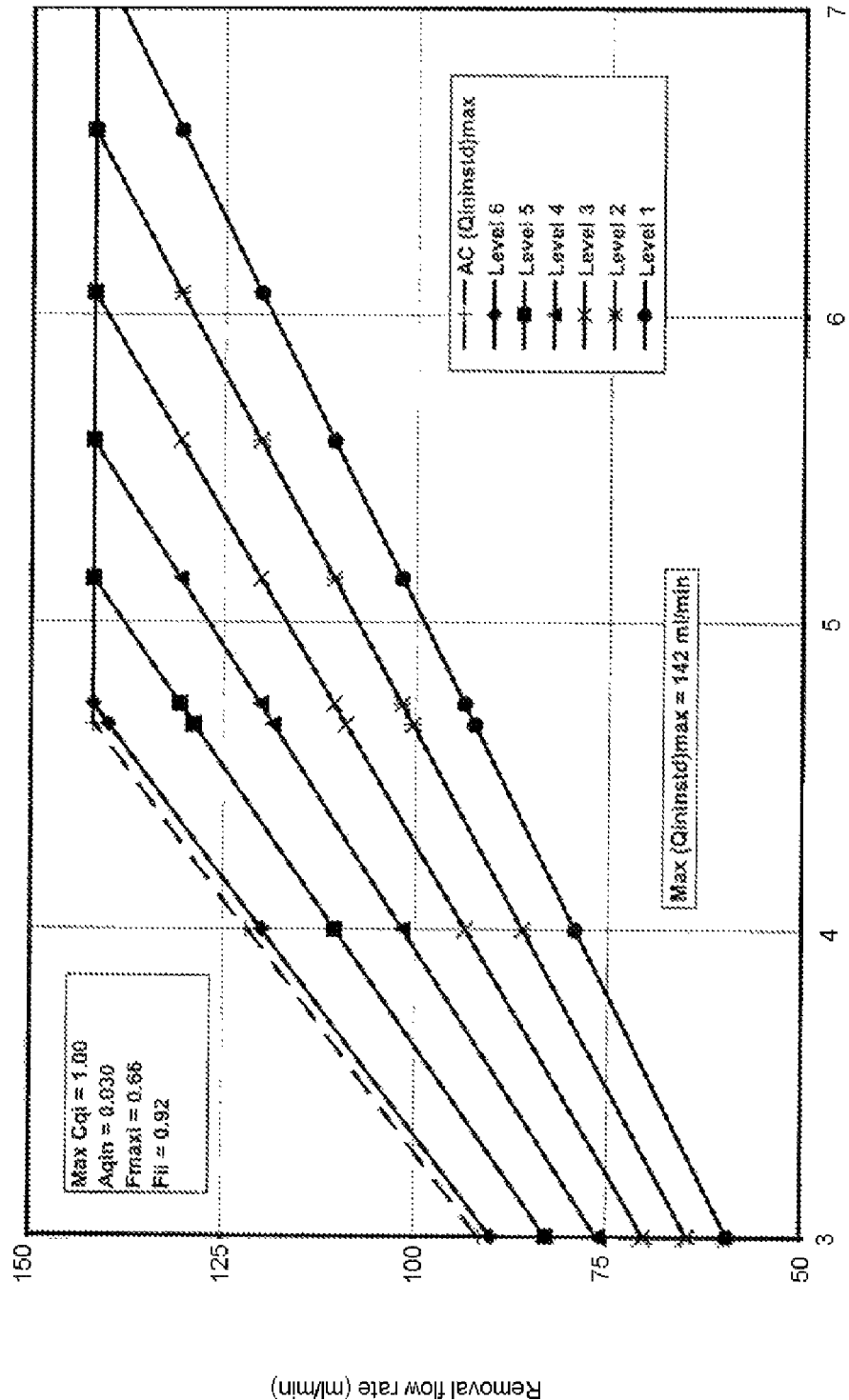
FIG. 3A shows plots of maximum removal flow rate (ml min.$^{-1}$) as a function total blood volume (liter) for operation levels 1 through 6
Figure 3B:
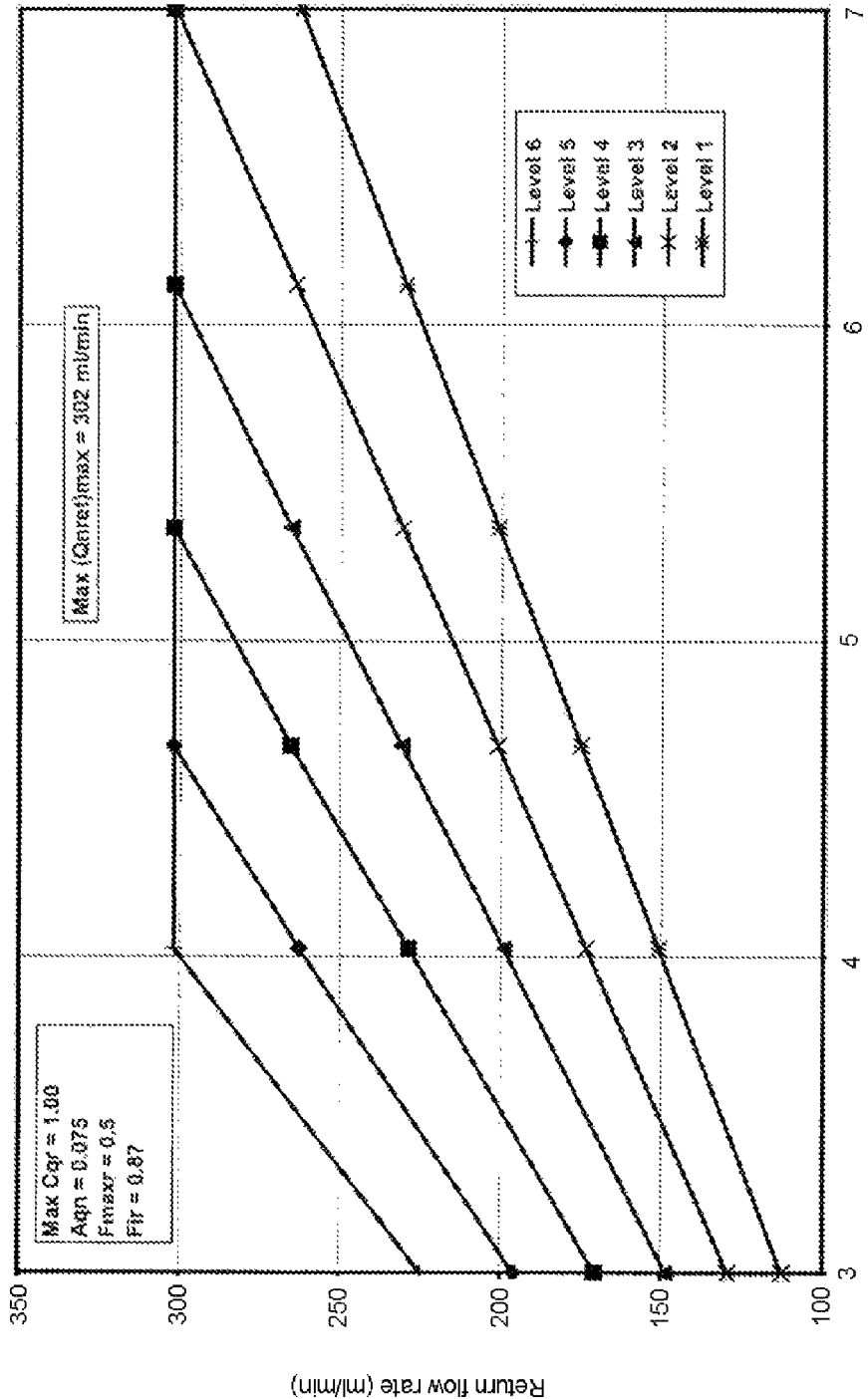
FIG. 3B shows plots of maximum return flow rate (ml min.$^{-1}$) as a function total blood volume (liter) for operation levels 1 through 6.

FIGS. 3A and 3B present a graphical representation of Equations 7 and 8. Specifically, FIG. 3A shows plots of maximum removal flow rate (ml min.$^{-1}$) as a function total blood volume (liter) for operation levels 1 through 6 and FIG. 3B shows plots of maximum return flow rate (ml min.$^{-1}$) as a function total blood volume (liter) for operation levels 1 through 6. As illustrated in FIG. 3A, the maximum removal flow rates increase with increasing total blood volume until reaching a value equal to approximately 142 ml, wherein the maximum removal flow rate is held constant. As illustrated FIG. 3B, the maximum return flow rates increase with increasing total blood volume until reaching a value equal to approximately 302 ml min.$^{-1}$ wherein the maximum return flow rate is held constant. The maximum removal flow rate and return flow rate profiles shown in FIGS. 3A and 3B are beneficial because they limit these rates to values wherein minimal hemolysis occurs. For example, limiting the maximum removal flow rate to a value less than about 142 ml min.$^{-1}$ and the maximum return flow rate to a value less than about 302 ml min.$^{-1}$ results in less than 0.1% hemolysis of the blood and/or blood components undergoing processing.

Methods and devices of the present invention having return flow rates, removal flow rates or both which are derived from a subject's total blood volume are beneficial because they substantially reduce the risk and incidence of blood vessel infiltration and hematoma. Particularly, removal flow rates derived from total blood volume reduce blood vessel infiltration caused by vein collapse and return flow rates derived from total blood volume reduce blood vessel infiltration caused by overexpansion blood vessel walls and subsequent perforation (i.e. vein blow out). For example, conventional extracorporeal blood processing methods typically have an incidence of vein infiltration greater than or equal to about 4.5%. In contrast, the methods of the present invention result in an incidence of vein infiltration less than or equal to about 3.0%. This decrease in the incidence of vein infiltration corresponds to an improvement over conventional blood processing methods greater than about 30%. The decrease in vein infiltration achieved by the present methods and devices is beneficial because it substantially increases patient or donor satisfaction and physical comfort. In addition, the decrease in vein infiltration achieved by the present methods and devices improves overall processing efficiency because it reduces the occurrence of processing delays and operator intervention associated vein infiltration. Finally, the decrease in vein infiltration achieved by the present methods and devices reduces patient or donor injuries resulting from processing, such as hematomas, damage to blood vessel tissue and changes in blood pressure which may trigger more serious health related injuries.

In another exemplary embodiment, the present invention provides blood processing methods and devices having a fraction by volume of the removed blood or anticoagulant-treated removed blood corresponding to collected components selected to achieve high purities of collected components and optimal blood processing efficiency. In the present invention, recirculation of a portion of the removed blood through the blood separation system is beneficial for maintaining quasi-steady state flow conditions during the return cycle, which in turns results in more effective and efficient blood separation and collection. Collection of non-red blood cell blood components, however, results in an enhancement of the hematocrit of the removed blood corresponding to the recirculated component due to mass balance. If the hematocrit of the recirculated component is too large, recirculation of the enhanced hematocrit recirculated component may lead to contamination of collected components with red blood cells, commonly referred to as spillover. The present methods and devices provide for selection of the fraction by volume of removed blood corresponding to collected component, the volume of collected components and/or removal flow rates of collected components, which minimize the risk of red blood cell contamination and optimize collection efficiency.

In an exemplary embodiment, the fraction by volume of removed blood corresponding to one or more collected components is selected such that the weighted average of the hematocrit of the removed blood or anticoagulant-treated removed blood ($H_{rem}$) and the hematocrit of the enhanced hematocrit recirculated component ($H_{recir}$) is less than or equal to about 70%. In an alternative embodiment, the fraction by volume of removed blood corresponding to one or more collected components is selected such that the weighted average of the hematocrit of the removed blood or anticoagulant-treated removed blood ($H_{rem}$) and the hematocrit of the enhanced hematocrit recirculated component ($H_{recir}$) is less than or equal to about 65%. In another embodiment, the fraction by volume of removed blood corresponding to one or more collected components is selected such that the weighted average of the hematocrit of the removed blood or the anticoagulant-treated removed blood ($H_{rem}$) and the hematocrit of the enhanced hematocrit recirculated component ($H_{recir}$) is less than or equal to $$\left(1 - \left(\frac{H_{rem}}{H_{recir}}\right)\right).$$

In these embodiments of the present invention, the weighted average of the anticoagulant-treated removed blood and the enhanced hematocrit recirculated component may be defined by the expression:

$$\overline{H} = H_{rem}\left(\frac{V_{rem}}{V_{rem} + V_{recir}}\right) + H_{recir}\left(\frac{V_{recir}}{V_{rem} + V_{recir}}\right) \quad (11)$$

wherein $\overline{H}$ is the weighted average of the anticoagulant-treated removed blood and the enhanced hematocrit recirculated component, $H_{rem}$ is the hematocrit of the anticoagulant-treated removed blood, $V_{rem}$ is the volume of the anticoagulant-treated removed blood, conducted through the blood separation system, $H_{recir}$ is the hematocrit of the recirculated component and $V_{rem}$ is the volume of the volume of the recirculated component conducted through the blood separation system.

In another embodiment, the fraction by volume of removed blood corresponding to one or more collect components is a function of the duty cycle of the blood processing system and the ratio of $H_{rem}/H_{recir}$. In an exemplary embodiment providing high purities of collected non-red blood cell components and optimal blood processing efficiency, the fraction by volume of removed blood corresponding to collected components is provide by the expressions:

$$F_{cmax} = \left( \frac{\left( \left[ A^2 + \frac{(1-z)(1-b)}{(1-D)} \right]^{0.5} - A \right)}{(1-z)} \right); \quad (12)$$

$$b = \frac{H_{rem}}{H_{recir}}; \quad (13)$$

$$D = \frac{t_{draw}}{(t_{draw} + t_{ret})}; \quad (14)$$

$$A = \left( \frac{\left(\frac{1}{1-D}\right) + \left(\frac{C_r}{D}\right)}{2} \right); \quad (15)$$

$$C_r = \left( \frac{R_{ret}}{R_{draw}} \right); \quad (16)$$

$$z = \left( \frac{V_{svnr}}{V_{svn}} \right). \quad (17)$$

In Equations 12 to 17, $t_{draw}$ is the time corresponding to the draw cycle, $t_{ret}$ is the time corresponding to the return cycle, $R_{draw}$ is the flow rate of the inlet pump during the draw cycle, $R_{ret}$ is the flow rate of the inlet pump during the return cycle, $V_{svn}$ is the volume of anticoagulant-treated removed blood required to fill the fixed volume return reservoir and $V_{svnr}$ is the volume of the recirculated component. In an exemplary embodiment of the present invention, D is a value selected over the range of about 0.5 to about 1, preferably a value of 0.7, ($R_{ret}/R_{draw}$) is a value selected over the range of about 0.1 to about 1, preferably a value of 0.5, and ($V_{svnr}/V_{svn}$) is a value selected over the range of about 0.03 to about 0.05.

As illustrated by Equations 12 to 17, Fcmax is coupled to several variables, the most important being (Hrem/Hrecir) and D. First, Fcmax is coupled to (Hrem/Hrecir). Typically, the Hrecir parameter is a value established by the blood separation system or blood processing procedure employed. In addition, Hrecir is directly related to Fcmax by mass balance, wherein larger values of Fcmax result in larger values of Hrecir and smaller values of Fcmax in smaller values of Hrecir. On the other hand, Hrem is independent of Fcmax and varies with the physiological characteristics of the patient or donor, typically varying from about 35% to about 55%. In the context of therapeutic applications of the present methods and devices, Hrem may be as high as 80%. Second, Fcmax is strongly coupled to duty cycle (D). A larger value of duty cycle corresponds to blood processing having a longer draw cycle than return cycle. In this instance, less recirculated component is recirculated through the blood separation system and, thus, Fcmax may be a larger value without substantial risk of contamination of collected components with red blood cells. In contrast, a smaller value of duty cycle corresponds to blood processing having draw and return cycles that are more similar in value. In this instance, more recirculated component is recirculated through the blood separation system and, thus, Fcmax cannot assume larger values without substantially increasing the risk of contamination of collected components with red blood cells. Finally, Fcmax is coupled to (Rret/Rdraw). As predicted in Equations 12-17, higher values of Fcmax are associated with lower values of (Rret/Rdraw) because less recirculated component is recirculated when Rret is low with respect to Rdraw. As will be appreciated by one of skill in the art of fluid mechanics, Fcmax is weakly coupled to (Vsvnr/Vsvn). Therefore, the present invention may be practiced with a certain degree of effectiveness by ignoring the (1−z) terms in Equation 12.

Figure 4:
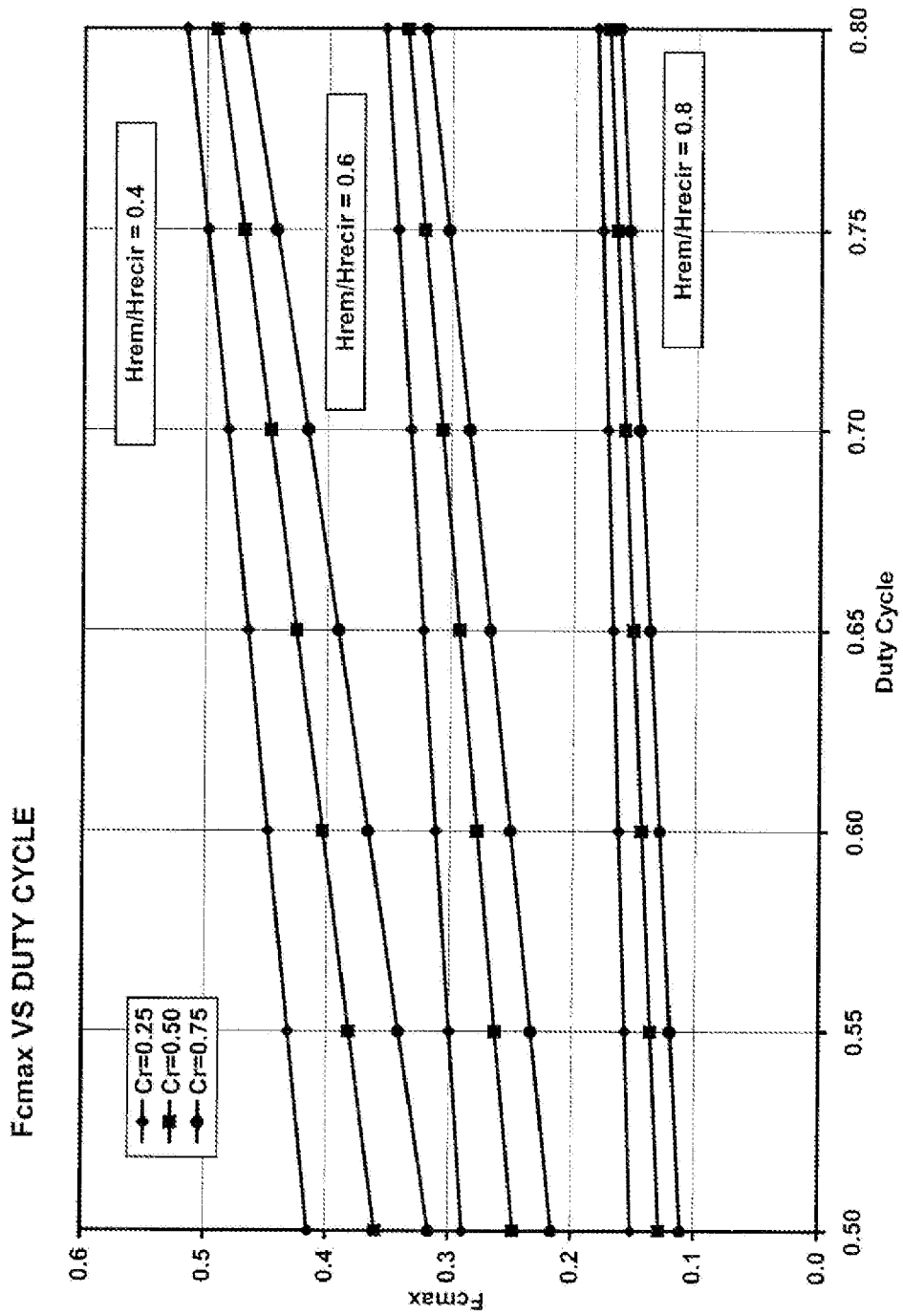
FIG. 4 provides plots of $F_{cmax}$ verses duty cycle corresponding to three values of ($H_{rem}/H_{recir}$), 0.4 (top), 0.6 (middle) and 0.8 (bottom), and three values of Cr, 0.25 (diamonds), 0.50 (squares) and 0.75 (circles).

FIG. 4 provides a graphical representation of Equations 12 to 17 and illustrates the dependence of Fcmax on duty cycle (D). Specifically, FIG. 4 provides plots of Fcmax verses duty cycle corresponding to three values of Hrem/Hrecir, 0.4 (top), 0.6 (middle) and 0.8 (bottom), and three values of Cr, 0.25 (diamonds), 0.50 (squares) and 0.75 (circles). As shown in FIG. 4, Fcmax increases with duty cycle for a selected value of Hrem/Hrecir and Fcmax decreases with Cr for a selected value of Hrem/Hrecir.

Blood processing methods and devices having a fraction by volume of the removed blood corresponding to collected components established by Equations 12 to 17 provide improved blood collection efficiency compared to convention extracorporeal blood processing methods. Particularly, these methods optimize collection efficiency by providing the maximum volume of collected components, while maintaining separation conditions in the blood processing system necessary for achieving high purity collected blood components.

Flow rates in the present invention, particularly removal flow rates and return flow rates, may be provided and controlled by any means known in the art of fluid mechanics. Exemplary means of providing and controlling flow rates during blood processing include the use of peristaltic pumps, whereby blood and/or blood components contained in flexible or deformable tubing is conducted by successive contraction and expansion of the walls of the tubing resulting in peristaltic movement. Peristaltic pumps are preferred for many applications of the present invention because they are capable of providing the necessary fluid flows without physically contacting the blood and blood components undergoing processing. Therefore, peristaltic pumps are ideally suited for applications requiring sterile conditions, such as blood donation and therapeutic apheresis techniques. The present invention may be practiced with other pumps and flow control devices known in the art of fluid mechanics including, but not limited to, constant volume fluid pumps, fluid displacement pumps, diaphragm pumps, rotary pumps, valves, control values, switching valves, shut off valves and flow controllers.

All references cited in this application are hereby incorporated in their entireties by reference herein to the extent that they are not inconsistent with the disclosure in this application. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques specifically described herein are intended to be encompassed by this invention.

We claim:

1. A method of processing blood, comprising the steps of:
   determining the total blood volume of a subject undergoing a blood processing procedure;
   removing blood from said subject at a selected removal flow rate thereby generating removed blood, wherein said selected removal flow rate is adjusted during operation of the blood processing procedure based on said total blood volume;
   processing said removed blood, thereby generating processed blood including at least one return component; and
   returning at least a portion of said return component to said subject at a return flow rate.

2. A method of processing blood, comprising the steps of:
   determining the total blood volume of a subject undergoing a blood processing procedure;
   removing blood from said subject, thereby generating removed blood;
   processing said removed blood, thereby generating processed blood including at least one return component; and
   returning at least a portion of said return component to said subject at a selected return flow rate, wherein said selected return flow rate is adjusted during operation of the blood processing procedure based on said total blood volume of said subject.

3. A method of processing blood, comprising the steps of:
   determining the total blood volume of a subject undergoing a blood processing procedure;
   removing blood from said subject at a removal flow rate thereby generating removed blood, wherein said removal flow rate is adjusted during operation of the blood processing procedure based on said total blood volume;
   processing said removed blood, thereby generating processed blood including at least one return component; and
   returning at least a portion of said return component to said subject at a return flow rate, wherein said return flow rate is adjusted during operation of the blood processing procedure based on said total blood volume of said subject.

4. The method of claim 3 wherein said return and removal flow rates are linearly correlated to said total blood volume of said subject.

5. The method of claim 4 wherein said return and removal flow rates increase with increasing total blood volume of said subject.

6. The method of claim 3 wherein said removal flow rate is provided by the expression:

$$Z_{rem}=(M_{rem})\times(V_B)\leq Q_{rem\,max},$$

wherein $Z_{rem}$ is the removal flow rate, $M_{rem}$ is a removal flow rate slope, $V_B$ is the total blood volume of said subject and $Q_{rem\,max}$ is a maximum removal flow rate.

7. The method of claim 6 wherein $M_{rem}$ is a value selected from the range of about 0.0066 min$^{-1}$ and about 0.05 min$^{-1}$ and $Q_{rem\,max}$ is a value selected from the range of about 100 ml min$^{-1}$ to about 160 ml min$^{-1}$.

8. The method of claim 7 wherein $Q_{rem\,max}$ is about 142 ml min$^{-1}$.

9. The method of claim 6 wherein $M_{rem}$ is provided by the expression:

$$M_{rem}=(C_{qr})\times(A_{rem})$$

wherein $C_{qr}$ is a selectably adjustable processing rate parameter, $A_{rem}$ is a constant having a value selected from the range of about 0.01 min$^{-1}$ to about 0.05 min$^{-1}$ wherein the value of $C_{qr}$ is selected to avoid the occurrence of infiltration of an access blood vessel of said subject.

10. The method of claim 3 wherein said return flow rate is provided by the expression:

$$Z_{ret}=(M_{ret})\times(V_B)\leq Q_{ret\,max}$$

wherein $Z_{ret}$ is the return flow rate, $M_{ret}$ is a return flow rate slope, $V_B$ is the total blood volume of said subject, and $Q_{ret\,max}$ is a maximum return flow rate.

11. The method of claim 10 wherein $M_{ret}$ is a value selected from the range of about 0.025 min$^{-1}$ and about 0.200 min$^{-1}$ and $Q_{ret\,max}$ is a value selected from the range of about 200 ml min$^{-1}$ and about 400 ml min$^{-1}$.

12. The method of claim 11 wherein $Q_{ret\,max}$ is about 302 ml min$^{-1}$.

13. The method of claim 10 wherein $M_{ret}$ is provided by the expressions:

$$M_{ret}=(C_{qr})\times(A_{ret}),$$

wherein $C_{qr}$ is a selectably adjustable parameter, $A_{ret}$ is a constant having a value selected from the range of about 0.05 min$^{-1}$ to about 0.20 min$^{-1}$, and wherein the value of $C_{qr}$ is selected to avoid discomfort of said subject.

14. The method of claim 3 wherein said subject is a human male and said total blood volume is determined using the expression:

$$V_B=604+(3.669\times10^{-4})(L^3)+(32.187)(W),$$

wherein L is the length of the subject in units of centimeters, W is the weight of the subject in units of kilograms and $V_B$ is total blood volume in units of milliliters.

15. The method of claim 3 wherein said subject is a human female and said total blood volume is determined using the expression:

$$V_B=183+(3.561\times10^{-4})(L^3)+(33.069)(W),$$

wherein L is the length of the subject in units of centimeters, W is the weight of the subject in units of kilograms and $V_B$ is total blood volume in units of milliliters.

16. The method of claim 3 wherein said removed blood is removed through an access needle and said return component is returned through said access needle.

17. The method of claim 3 wherein said removed blood is removed through a first access needle and said return component is returned through a second access needle.

18. The method of claim 3 wherein said blood is removed during a draw cycle and said portion of said return component is returned during a return cycle.

19. The method of claim 18 further comprising the step of sequentially repeating said draw and return cycles for a selected blood processing time.

20. The method of claim 3 wherein said processing step comprises the steps of:
    separating said removed blood into a plurality of separated blood components including at least one collect component and said return component; and collecting a collect component.

21. The method of claim 20 wherein said separating step comprises conducting said removed blood through a density centrifuge system.

22. The method of claim 20 wherein said separating step comprises conducting said removed blood through a centrifugal elutriation system.

23. The method of claim 20 wherein said collect component is plasma.

24. The method of claim 20 wherein said collect component is red blood cells.

25. The method of claim 20 wherein said collect component is white blood cells.

26. The method of claim 20 wherein said collect component is platelets.

27. The method of claim 3, further comprising the step of:
sequentially repeating said steps of removing blood and of returning blood for a selected blood processing time, whereby the removal flow rate is increased each draw cycle by a selected flow adjustment increment.

* * * * *